United States Patent
Bayer et al.

(10) Patent No.: US 10,124,118 B2
(45) Date of Patent: Nov. 13, 2018

(54) DRIVE MECHANISM OF A DRUG DELIVERY DEVICE

(71) Applicant: Sanofi, Paris (FR)

(72) Inventors: Stefan Bayer, Würselen (DE); Daniel Berning, Baesweiler (DE); Philippe Blank, Düsseldorf (DE); Wolfgang Pelzer, Kreuzau (DE); Björn Wilden, Simmerath (DE)

(73) Assignee: Sanofi, Paris (FR)

( * ) Notice: Subject to any disclaimer, the term of this patent is extended or adjusted under 35 U.S.C. 154(b) by 439 days.

(21) Appl. No.: 14/782,723

(22) PCT Filed: Apr. 8, 2014

(86) PCT No.: PCT/EP2014/056974
§ 371 (c)(1),
(2) Date: Oct. 6, 2015

(87) PCT Pub. No.: WO2014/166896
PCT Pub. Date: Oct. 16, 2014

(65) Prior Publication Data
US 2016/0067415 A1    Mar. 10, 2016

(30) Foreign Application Priority Data
Apr. 10, 2013   (EP) .................. 13163073

(51) Int. Cl.
  *A61M 5/315*   (2006.01)
  *A61M 5/20*    (2006.01)
  *A61M 5/31*    (2006.01)

(52) U.S. Cl.
  CPC .......... *A61M 5/31541* (2013.01); *A61M 5/20* (2013.01); *A61M 5/31553* (2013.01);
  (Continued)

(58) Field of Classification Search
  CPC ...... A61M 5/31541; A61M 2005/3154; A61M 5/31568; A61M 5/3157; A61M 5/31583
  See application file for complete search history.

(56) References Cited

U.S. PATENT DOCUMENTS

| | | | |
|---|---|---|---|
| 2006/0153693 A1* | 7/2006 | Fiechter | A61M 5/31553 417/63 |
| 2008/0306445 A1 | 12/2008 | Burren et al. | |

(Continued)

FOREIGN PATENT DOCUMENTS

| | | |
|---|---|---|
| WO | WO 2004/020028 | 3/2004 |
| WO | WO 2004/078239 | 9/2004 |
| WO | WO 2006/079481 | 8/2006 |

OTHER PUBLICATIONS

International Preliminary Report on Patentability in International Application No. PCT/EP2014/056974, dated Oct. 13, 2015, 8 pages.

(Continued)

*Primary Examiner* — Andrew Gilbert
*Assistant Examiner* — John Doubrava
(74) *Attorney, Agent, or Firm* — Fish & Richardson P.C.

(57) ABSTRACT

A drive mechanism of a drug delivery device for dispensing of a dose of a medicament includes a housing extending in an axial direction, a piston rod to operably engage with a piston of a cartridge to displace the piston in an axial distal direction, and a drive sleeve extending in the axial direction and being rotatable in a dose incrementing direction against the action of a spring enclosing at least an axial portion of the drive sleeve. The drive mechanism further includes a dose limiting member threadedly engaged with the drive sleeve, rotatably locked to the housing and at least partially extending radially between the drive sleeve and the spring, and at least one stop located on at least one of dose limiting
(Continued)

member and drive sleeve for limiting an axial displacement of the dose limiting member relative to the drive sleeve.

22 Claims, 14 Drawing Sheets

(52) U.S. Cl.
CPC ....... *A61M 5/31583* (2013.01); *A61M 5/3157* (2013.01); *A61M 2005/3126* (2013.01); *A61M 2005/3154* (2013.01); *A61M 2205/581* (2013.01); *A61M 2205/582* (2013.01)

(56) References Cited

U.S. PATENT DOCUMENTS

| | | | |
|---|---|---|---|
| 2011/0054412 A1* | 3/2011 | Eich | A61M 5/20 604/207 |
| 2011/0283997 A1 | 11/2011 | Walsh et al. | |
| 2012/0245532 A1* | 9/2012 | Frantz | A61M 5/31551 604/211 |

OTHER PUBLICATIONS

International Search Report and Written Opinion in International Application No. PCT/EP2014/056974, dated Jun. 4, 2014, 14 pages.
Rote Liste, "50. Hypophysen-, Hypothalamushormone, andere regulatorische Peptide u. ihre Hemmstoffe," Chapter 50, ed. 2008, 20 pages.

* cited by examiner

A-A

B-B

C-C

D-D

E-E

F-F

G-G

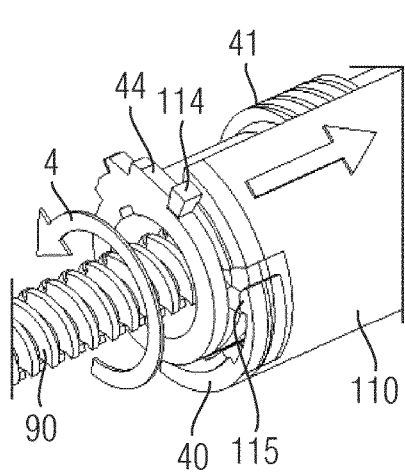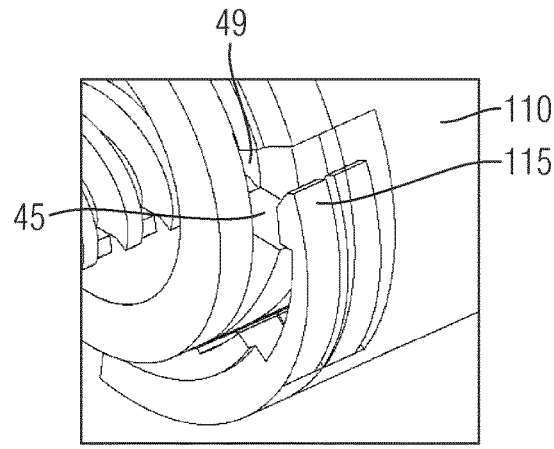
Fig. 24  Fig. 24a
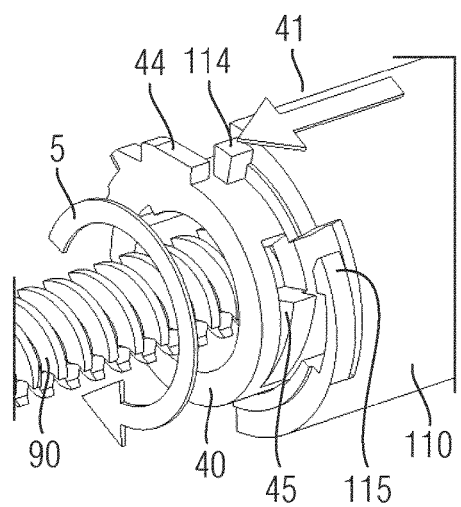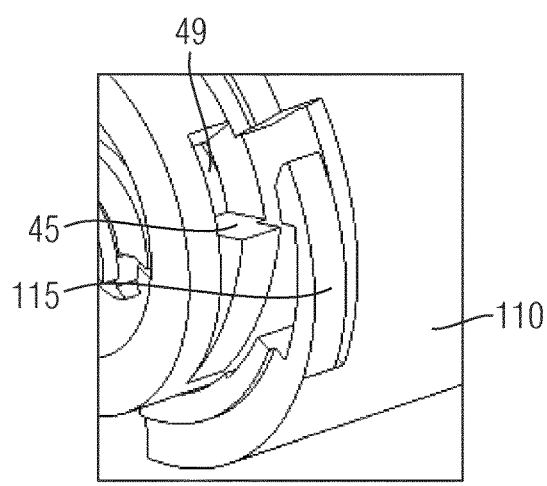
Fig. 25  Fig. 25a

DRIVE MECHANISM OF A DRUG DELIVERY DEVICE

CROSS-REFERENCE TO RELATED APPLICATION

This application is a national stage application under 35 U.S.C. § 371 of International Patent Application No. PCT/EP2014/056974, filed on Apr. 8, 2014, which claims priority to EP 13163073.3, filed on Apr. 10, 2013. The entire contents of each of the foregoing applications are incorporated herein by reference.

TECHNICAL FIELD

The present disclosure relates to a drive mechanism for a drug delivery device and to a respective drug delivery device. In particular, the disclosure relates to an injection device such like a pen-type injector inter alia comprising a single and/or a last-dose limiting mechanism and further comprising a comparatively large dose indicating display.

BACKGROUND

Drug delivery devices for setting and dispensing a single or multiple doses of a liquid medicament are as such well-known in the art. Generally, such devices have substantially a similar purpose as that of an ordinary syringe.

Drug delivery devices, in particular pen-type injectors have to meet a number of user-specific requirements. For instance, with patient's suffering chronic diseases, such like diabetes, the patient may be physically infirm and may also have impaired vision. Suitable drug delivery devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing or a particular cartridge holder, which is adapted to receive a cartridge at least partially filled with the medicament to be dispensed. The device further comprises a drive mechanism, usually having a displaceable piston rod which is adapted to operably engage with a piston of the cartridge. By means of the drive mechanism and its piston rod, the piston of the cartridge is displaceable in a distal or dispensing direction and may therefore expel a predefined amount of the medicament via a piercing assembly, which is to be releasably coupled with a distal end section of the housing of the drug delivery device.

The medicament to be dispensed by the drug delivery device is provided and contained in a multi-dose cartridge. Such cartridges typically comprise a vitreous barrel sealed in distal direction by means of a pierceable seal and being further sealed in proximal direction by the piston. With reusable drug delivery devices an empty cartridge is replaceable by a new one. In contrast to that, drug delivery devices of disposable type are to be entirely discarded when the medicament in the cartridge has been completely dispensed or used-up.

With such multi-dose drug delivery devices at least a last dose limiting mechanism is required to inhibit setting of a dose exceeding the amount of medicament left in the cartridge. This is to avoid a potentially dangerous situation for the user believing that a set dose is entirely injected. There already exist some drug delivery devices with end-of-content mechanisms or last dose mechanisms.

Drug delivery devices such like pen type injectors also provide a dose indicating mechanism which is operable to display the size of a set dose to a user. Typically, the housing of such drug delivery devices comprises a dose indicating window in which a number representing the size of the dose shows up.

Especially with elderly patients or users suffering impaired vision, reading of such dose indicating numbers is sometimes difficult. With devices adapted for injection of e.g. insulin, typical dose sizes may vary between 0 and 120 I.U. (International Units) of insulin. Due to the rather compact design and limited geometrical dimensions of typical drug delivery devices the size of such dose indicating numbers is fairly small. For visually impaired persons correct reading of comparatively tiny numbers may therefore be rather difficult. However, since such drug delivery devices are intended for self-medication treatment, it is of importance, that the user is able to correctly determine the size of dose actually set.

SUMMARY

Certain aspects of the present invention avoid disadvantages of known drug delivery devices and provide drive mechanisms of drug delivery devices allowing for an intuitive operation, both for setting and for dispensing of a dose. Some aspects provide dose indicating mechanisms which are easy and unequivocal to read even for persons suffering impaired vision.

Some aspects provide a drive mechanism of a drug delivery device for setting and dispensing of a dose of a medicament and further featuring a single and/or a last dose limiting mechanism.

Moreover, in certain aspects, the drive mechanism is rather compact to limit the overall size of the drug delivery device.

Some aspects provide a drug delivery device comprising such a drive mechanism and comprising a cartridge sealed with a piston and being operably engaged with a piston rod of such drive mechanism. In certain aspects, the drug delivery device is rather easy and intuitive to handle.

In a first aspect a drive mechanism of a drug delivery device is provided for dispensing of a dose of a medicament. The drive mechanism comprises an elongated housing extending in an axial direction. The housing is of substantially tubular or cylindrical shape that allows gripping and operating of the drive mechanism and of the drug delivery device by only one hand of a user.

The drive mechanism further comprises a piston rod to operably engage with a piston of a cartridge containing the medicament to be dispensed by the drive mechanism. The cartridge comprises a piston at its proximal end, which, by means of a displacement in axial distal direction serves to expel an amount of the medicament from the cartridge. The piston typically seals the cartridge in axial proximal direction.

The piston rod of the drive mechanism serves to displace the piston of the cartridge in axial distal direction for expelling a predefined amount of the medicament from the cartridge. Hence, the piston rod is operable to apply distally-directed thrust or pressure to the piston of the cartridge for displacing the same in distal direction for a predetermined distance that corresponds to a respective amount or dose of the medicament to be dispensed.

The drive mechanism further comprises a drive sleeve extending in axial direction and being rotatably supported in the housing. Typically, the drive sleeve is rotatable with regard to an axis of rotation substantially coinciding with the axial direction of the elongated housing. Moreover, the drive sleeve is rotatable in a dose incrementing direction against the action of a spring, in particular for setting of a dose during a dose setting procedure. By rotating the drive sleeve in a dose incrementing direction, said spring, which is typically directly engaged with the drive sleeve, can be biased in order to store mechanical energy.

Moreover, the spring encloses or surrounds at least an axial portion of the drive sleeve. Typically, the spring comprises a helical spring wound around the axial portion of the drive sleeve in a screw-like or helical way.

After setting of a dose the drive sleeve may rotate in an opposite, hence dose decrementing direction under the action of said spring for driving the piston rod in distal direction during a dose dispensing procedure. Typically, the drive sleeve is alternately operably engageable and operably disengageable to and from the piston rod for dispensing and for setting of a dose, respectively. During a dose setting procedure, the piston rod remains substantially stationary with respect to the housing while the drive sleeve, operably disconnected and released from the piston rod is rotatable relative to the housing and hence relative to the piston rod.

The drive mechanism further comprises a dose limiting member threadedly engaged with the drive sleeve and being further rotatably locked to the housing. Said dose limiting member at least partially extends radially between the drive sleeve and the surrounding spring. Typically, the dose limiting member extends radially inwardly from the spring and radially outwardly with regard to the drive sleeve. For rotatably locking the drive sleeve to the housing at least a portion of the drive sleeve is directly engageable with an inside facing sidewall portion of the housing. Typically, a portion of the dose limiting member engaging with the housing may axially protrude from an axial end section of the spring.

At least a portion of the dose limiting member is located radially between the drive sleeve and the spring, while another portion of the dose limiting member is rotatably locked to the housing and extends radially beyond the circumference of the spring. Hence, as seen in a radial direction, the a first axial portion of the dose limiting member is located radially between the drive sleeve and the spring while a second axial portion of the dose limiting member is located axially offset from an axial end of the spring. It is in particular the second axial portion that is rotatably locked to the housing.

Moreover, the drive mechanism comprises at least one stop located on at least one of dose limiting member and drive sleeve for limiting an axial displacement of the dose limiting member relative to the drive sleeve.

Since the drive sleeve is rotatably supported in the housing and since the drive sleeve is threadedly engaged with the dose limiting member a rotation of the drive sleeve relative to the housing leads to an axial displacement of the dose limiting member relative to the housing and relative to the drive sleeve because the dose limiting member is rotatably locked to the housing. Hence, the dose limiting member is free to slide in axial direction relative to the housing. The dose limiting member may therefore splined with the housing.

Dose incrementing and/or dose decrementing rotation of the dose limiting member may therefore be always accompanied with an axial displacement of the dose limiting member relative to the housing and/or relative to the drive sleeve, in particular when the drive sleeve is axially constrained or axially fixed in the housing. By providing at least one stop on or at the dose limiting member and/or on or at the drive sleeve, a relative rotation of dose limiting member and drive sleeve may be blocked when said stop, e.g. of the dose limiting member, engages with a corresponding stop of the drive sleeve.

When mutually corresponding stops of dose limiting member and drive sleeve mutually engage, a further rotation of the drive sleeve relative to the housing may be blocked by the dose limiting member. In this way, a dose limiting mechanism can be provided in order to inhibit setting of a dose exceeding a maximum dose size of e.g. 120 IU.

The dose limiting member may not only be operable to limit the size of a maximum dose but may also be operable to prevent setting of a dose of less than zero. Moreover, since the drive sleeve may rotate in a dose decrementing direction during dose dispensing, a zero dose configuration provided by a particular zero dose stop may provide and determine a well-defined end of injection configuration of the drive mechanism.

The at least partially interleaved configuration of drive sleeve, spring and dose limiting member is particularly advantageous to realize a compact design of the drive mechanism. By at least partially sandwiching the dose limiting member between the drive sleeve and the surrounding spring, axial dimensions of the drive mechanism and hence axial dimensions of a drug delivery device can be effectively minimized.

According to an embodiment, the dose limiting member and the housing comprise at least one radially outwardly extending protrusion engaged with a correspondingly shaped and axially extending groove. Typically, the radially outwardly extending protrusion is located on the outer circumference of the dose limiting member while the corresponding groove of recess is provided at an inside facing sidewall portion of the housing, which may be at least partially of substantially tubular shape. Alternatively, it is also conceivable, that the housing comprises a radially inwardly extending ridge or an axially elongated protrusion to engage with a correspondingly shaped notch or groove of the dose limiting member.

By means of at least one radially extending protrusion engaged with a correspondingly shaped groove a splined engagement of the dose limiting member and the housing can be attained. Hence, the dose limiting member may be axially slidably displaced relative to the housing while dose limiting member and housing are hindered to mutually rotate.

According to another embodiment, the at least one radially outwardly extending protrusion of the dose limiting member is located axially offset from an axial end of the spring. Here, the at least one radially outwardly extending protrusion of the dose limiting member may be located at an axial end of the dose limiting member which axially protrudes from the spring at least partially enclosing the dose limiting member and the drive sleeve. In this way, the radially outwardly extending protrusion of the dose limiting member may directly engage with the housing to provide a rotational interlock.

According to a further embodiment the dose limiting member comprises a shell-like profile extending only partially around the circumference of the drive sleeve. Moreover, oppositely located circumferential end sections thereof each comprise at least one radially outwardly extending protrusion, typically at an axial end portion of the dose limiting member which axially extends from the spring and which radially engages with the housing.

The shell-like profile may comprise an arc- or arcuate-shaped cross-section and may resemble a half nut. Hence, the dose limiting member may extend about 180° around the outer circumference of the drive sleeve. Such a shell-like profile is particularly beneficial for mutually assembling the dose limiting member, the spring and the drive sleeve. A shell-like profile is further beneficial in that the dose limiting member features two, e.g. diametrically oppositely located circumferential edges that may serve as a stop to engage with a correspondingly shaped stop of the drive sleeve.

Having two radially outwardly extending protrusions on oppositely located circumferential end sections of the shell-like dose limiting member a twofold splined engagement of the dose limiting member with the housing can be attained. Moreover, by translationally and axially guiding the dose limiting member in the housing by means of two positively engaged and radially outwardly extending protrusions of the dose limiting member, a particular smooth axial displacement of the dose limiting member relative to the housing substantially free of tilt or cant can be effectively provided.

Moreover, by a twofold axial guiding structure for the dose limiting member in the housing, a rather slack free guiding of the dose limiting member in the housing can be provided. In this way, a very robust and precise dose limiting configuration of the drive mechanism can be attained.

According to another embodiment the dose limiting member comprises a first radially inwardly extending stop to engage with a first radially outwardly extending stop of the drive sleeve. The first stop of the dose limiting member and the first stop of the drive sleeve are particularly adapted to mutually engage when the dose limiting member reaches a dose limiting configuration, either a zero dose configuration or a maximum dose configuration.

Radially extending stops of dose limiting member and/or of the drive sleeve are particularly adapted to bring drive sleeve and dose limiting member in mutual abutment and hence into a blocking configuration when the drive sleeve has rotated a particular angular distance. The mutually corresponding radially extending stops of dose limiting member and drive sleeve also extend in axial direction to provide a stop face extending in radial and axial direction. When getting in direct mutual abutment said radially and axially extending stop faces of the dose limiting members and the drive sleeve's first stops provide a rather well-defined, robust and precise mechanical engagement.

According to another embodiment the stop of the dose limiting member, in particular the first and radially inwardly extending stop of the dose limiting members is provided substantially midway between the oppositely located protrusions that are typically engaged with correspondingly shaped grooves of the housing. Said stop may therefore typically extend substantially midway between the circumferential edges or circumferential ends of the arc- or shell-like shaped dose limiting member.

When the dose limiting member is splined or rotatably locked with diametrically oppositely located radially outwardly extending protrusions with the housing, the radially inwardly extending first stop of the dose limiting member can be located midway therebetween. In this way, mechanical loads that may be transferred from the drive sleeve to the dose limiting member upon reaching of a stop configuration can be rather smoothly and homogeneously transferred to the housing. Arranging the first stop extending substantially midway between the circumferential edges of the dose limiting member is therefore beneficial in terms to reduce a potential tilt or cant of the dose limiting member.

According to a further embodiment, the radially outwardly extending stop of the drive sleeve is located axially offset from an outer thread of the drive sleeve. Moreover, the drive sleeve may only comprise a limited axial threaded portion, having an axial extension being much shorter compared to the axial extension of the dose limiting member. Typically, the axial extension of the dose limiting member's inner thread is almost as large as the distance the dose limiting member is allowed to travel between a proximal and a distal stop configuration, typically corresponding to a zero dose or to a maximum dose configuration, or vice versa.

Adjacent to the threaded portion the drive sleeve may comprise a substantially tubular and smooth outer surface that may serve as a support surface for the radially inwardly extending first stop of the dose limiting member. In this way, the dose limiting member can also be radially supported by means of the first stop sliding along the outer circumference of a non-threaded portion of the drive sleeve. When the dose limiting member's first stop is provided at an axial end thereof, such an axial end portion of the dose limiting member can be radially supported, thereby reducing a potential tilt, cant or slack of the dose limiting member relative to the drive sleeve.

According a further embodiment, the dose limiting member comprises a second stop at a circumferential and axial edge thereof to engage with a radially outwardly extending second stop of the drive sleeve. Also the second stop may be provided at an axial end of the drive sleeve. Furthermore, the second stops of dose limiting member and drive sleeve may be arranged in a radially overlapping or radially interleaved configuration with the spring. Hence, the portion of the dose limiting member featuring the second stop may extend radially between the drive sleeve and the spring.

Since the second stop of the dose limiting member is provided at a circumferential edge of its shell-like profile, the second stop may also effectively act as a radial stop. Hence, the edge features a stop face extending in radial as well as in axial direction. Alternatively, the second stop of the dose limiting member may also be provided elsewhere on the dose limiting member. Moreover, it is generally conceivable, that also the second stop of the dose limiting member extends radially inwardly to engage with a correspondingly shaped radially outwardly extending second stop of the drive sleeve.

In configurations, where the second stop of the dose limiting member does not radially inwardly extend from an inside facing sidewall portion of the dose limiting member it is generally conceivable, that the second stop of the dose limiting member is axially displaced into the region of the drive sleeve's outer thread. By not radially inwardly protruding from the shell-like profile of the dose limiting member, the second stop may neither interact nor engage with the drive sleeve's threaded portion.

Consequently, the dose limiting member may be axially displaced even into such positions, where the second stop radially overlaps with the drive sleeve's threaded portion. Such a configuration may be of particular benefit in order to further reduce the axial elongation of the drive mechanism and hence of the entire drug delivery device.

According to a further embodiment, first and second stops of the dose limiting member are located at opposite axial sections thereof. In particular, the second stop may be located at a distal end of the dose limiting member whereas the first stop may be located at a proximal end of the dose limiting member. Depending on the lead of the threaded engagement of dose limiting member and drive sleeve and further depending on whether the dose limiting member travels in distal or proximal direction during a dose incrementing or dose decrementing rotation of the drive sleeve, the zero dose configuration of the dose limiting member and the drive sleeve may coincide with a distal stop configuration of the dose limiting member and a maximum dose configuration may coincide or correspond with a proximal stop configuration of the dose limiting member, or vice versa.

In another embodiment, the second stop of the dose limiting member provided at a distal end thereof provides a zero dose stop whereas the first and proximally located stop of the dose limiting member serves as a maximum dose limiter, particularly adapted to limit the size of a single dose to be dispensed by means of a subsequent dose dispensing procedure.

In a further embodiment, the dose limiting member also comprises a resilient, circumferentially extending clicking member to audibly engage with a correspondingly shaped recess or ledge of the drive sleeve. Mutual and audible engagement of the clicking member and the drive sleeve's recess or ledge typically occurs before or when the dose limiting member's stop engages with a corresponding drive sleeve's stop. For instance, the clicking member of the dose limiting member may audibly engage with the drive sleeve just before or during the dose limiting member's second stop engages with the drive sleeve's second stop.

The resilient clicking member provides or comprises a kind of a pawl and is operable to generate a click noise or click sound when the dose limiting member reaches a zero dose configuration. Since the dose limiting member and the drive sleeve are subject to reversible or reversed displacements during dose incrementing and dose decrementing, the dose limiting member will always reach a zero dose configuration also at the end of a dose dispensing procedure. The clicking member then provides an audible feedback to the user, that the end of a dispensing procedure is reached or will be immediately reached.

According to another embodiment, the drive sleeve is further rotatably engaged with a dose indicating mechanism comprising a first spool and a second spool rotatably supported in the housing at a predefined distance in a substantially parallel orientation. Moreover, a dose indicating tape is coiled onto the second spool and is further fixed with an end to the outer circumference of the first spool. First and second spools typically extend in axial direction. First and second spools may further be oriented parallel with respect to each other. They may also extend substantially parallel to the longitudinal extension of the housing and/or to elongation of the piston rod and/or of the drive sleeve.

Moreover, first and second spools are arranged at a radial distance from the piston rod and/or from the drive sleeve. The spools are typically arranged radially outside the drive sleeve. They are positioned beneath and inside the housing and may be arranged in a substantially identical or at least partially overlapping axial position with respect to each other.

The dose indicating mechanism further comprises a dose indicating tape or belt which is coiled onto at least the second spool in an initial, hence in a zero dose configuration. Said dose indicating tape is further fixed with another end to an outer circumference of the first spool. The dose indicating tape therefore extends between the first and second spools and can be selectively coiled onto first and second spools in an alternating way. Unwinding the tape from the second spool comes along with coiling up the tape to the first spool and vice versa.

The dose indicating tape comprises a series of consecutive numbers representing the size of the dose actually set. The coils and the interconnected dose indicating tape extend beneath a dose indicating window of the housing in order to display the numbers printed on the tape when dialing or setting a dose of variable size.

During a dose setting procedure the first spool is typically rotatably coupled with the drive sleeve, thereby coiling up the dose indicating tape to the first spool to a certain extent. Depending on the numbers of revolutions of the first spool during a dose setting procedure and hence depending on the size of the dose to be set, the dose indicating tape will be transferred from the second spool towards the first spool. Since the dose indicating tape is alternately coiled up onto first and/or second spools, the tape itself can be rather long and may provide almost unlimited space for printing numbers thereon.

The numbers presented on the dose indicating tape may therefore be comparatively large, thereby providing a good visibility and a sufficient and unequivocal reading thereof, even by patients or users suffering impaired vision.

In a further embodiment, the second spool is rotatable against the action of a coil spring while the first spool is permanently rotatably engaged with the drive sleeve. Hence, unwinding the dose indicating tape from the second spool may only occur against the action of a respective spool spring. By means of the spool spring, the dose indicating tape can be sufficiently strained between first and second spools in order to stay free of any slacks, stripes or other deformations.

The spring spool particularly serves to return the dose indicating tape into the zero dose configuration, in which the dose indicating tape is almost entirely coiled up onto the second spool. Such a returning motion of the dose indicating tape typically occurs during a dose dispending procedure, in which the drive sleeve is free to rotate under the action of the helical spring, which is intended to be strained and biased during a dose setting procedure.

During a dose dispensing procedure, in which the second spool returns into an initial configuration under the action of the spool spring, the numbers of the dose indicating tape that will show up in the dose indicating window of the housing will decrement accordingly until a zero dose configuration is reached, in which second stops of the drive sleeve and the dose limiting member mutually engage.

In another embodiment, the drive sleeve is axially fixed relative to the housing. Hence, the drive sleeve is axially constrained in the housing. Moreover, the drive mechanism comprises at least one axially extending clutch member extending through the hollow drive sleeve. The clutch member is rotatably locked to the drive sleeve and is axially displaceable relative to the drive sleeve to selectively engage with a drive wheel or drive nut engaged with the piston rod for driving the same on distal direction, e.g. during dispensing of a dose.

Having a clutch member axially extending through the drive sleeve, the drive sleeve can be axially constrained and axially fixed in the housing. The clutch member is particularly adapted to transfer a torque to the drive sleeve during a dose setting procedure while the clutch member is operably disengageable from the drive sleeve during setting of a dose. In this way, a dose setting member, e.g. rotatably engaged with the clutch member can be disconnected from the drive sleeve at least during dose dispensing.

The clutch member therefore serves to switch the drive mechanism and the drug delivery device between a dose dispensing mode, in which the drive sleeve is operably engaged with the piston rod for driving the same in distal direction, and a dose setting mode, in which the drive sleeve is operably disengaged from the piston rod. A dose setting member to be actuated by a user is typically engageable with the drive sleeve during setting of a dose via the clutch member and may be operably disengaged from the drive sleeve during dose dispensing. In this way, the dose setting member will be substantially inoperable during a dose dispensing procedure.

In still another embodiment, the housing is adapted to receive a tubular insert providing a bearing portion for at least one of first and second spools. Moreover, the insert may also provide at least one of the axially extending grooves to engage with at least one of the dose limiting member's radially outwardly extending protrusions. For the purpose of assembling the various components of the drive mechanism, the insert may be provided as a separate piece allowing to set up a preassembly, e.g. a dose indicating preassembly.

For instance, the two spools of the dose indicating mechanism may be preassembled to or on the insert before the insert with the spools assembled thereon is introduced and positioned inside the housing of the drive mechanism and hence in the housing of the drug delivery device. In alternative embodiments it is also conceivable, that the insert is integrally formed with the housing or that the insert is designed as a part thereof. In this way, any reference made to the housing, in particular in regard to grooves, recesses or stops to engage with the dose limiting member may equally refer to respective components or structures of the insert, and vice versa.

Since the insert is adapted to be fixed in the housing and since the insert typically provides a mounting base for functional, hence displaceable or rotatable components of the drive mechanism, the insert effectively serves as a housing portion.

Another aspect of the invention also relates to a drug delivery device for dispensing of a dose of a medicament. The drug delivery device comprises a drive mechanism as described above and a cartridge at least partially filled with the medicament to be dispensed by the drug delivery device. The cartridge is arranged in the housing of the drive mechanism or in a cartridge holder of the drug delivery device which is fixed to the housing either releasably or non-releasably, e.g. in case of a disposable drug delivery device. Consequently, the drug delivery device comprises a cartridge holder to receive and to accommodate a cartridge filled with the medicament.

In case of a disposable drug delivery device the cartridge is not to be replaced when empty but the entire device is intended to be discarded. With a reusable device, the drive mechanism can be reset and an empty cartridge can be generally replaced by a new one.

Apart from that, the drug delivery device and the drive mechanism may comprise further functional components, such like an injection button, by way of which a user may trigger and control the drug delivery device and its drive mechanism for dispensing of a dose of the medicament.

In the present context, the distal direction points in the direction of the dispensing and of the device, where a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member is located at the proximal end of the drug delivery device, which is directly operable by a user to be rotated for setting of a dose and which is operable to be depressed in distal direction for dispensing of a dose.

Generally, by means of the spring element operably engaged with the drive member, a semi-automated drug delivery device can be provided. During a dose setting procedure the spring element can be strained or tensioned to such a degree, that a dose dispensing action of the drug delivery device can be exclusively driven by the relaxing action of the biased spring element. Hence, dose dispensing is completely governed by the action of a spring element previously tensioned and strained in a dose setting procedure.

The drive mechanism particularly serves to displace a piston rod in axial direction for the purpose of dispensing of a dose of a medicament. In addition, the drive mechanism typically comprises components which also form part of and have a function in at least one of the following mechanisms: a dose setting mechanism, a last dose limiting mechanism and a dose indicating mechanism. As will be apparent from the embodiments described herein various components of e.g. the drive mechanism also belong to at least one of the dose setting mechanism, the last dose limiting mechanism and/or to the dose indicating mechanism; and vice versa. Hence, the invention as described herein equally refers to and defines a drive mechanism, a dose setting mechanism, a last dose limiting mechanism and/or a dose indicating mechanism of a drug delivery device.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4 (1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4 (1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp (O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2) 25, Asp28] Exendin-4(S1-39)-(Lys)6-NH2,
H-Asn-(Glu)5-des Pro36, Pro37, Pro38 [Met(O)14, Trp (O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference signs used in the appended claims are not to be construed as limiting the scope of the present invention.

BRIEF DESCRIPTION OF THE DRAWINGS

In the following, an embodiment of the invention will be described by making reference to the drawings, in which:

FIG. 24 is a perspective view of the dose limiting member at the beginning of a dose incrementing displacement, FIG. 24a shows the clicking member of the dose limiting member according to FIG. 24, FIG. 25 shows the dose limiting member during a dose decrementing displacement, and FIG. 25a shows an enlarged view of the clicking member of the dose limiting member according to FIG. 25.

DETAILED DESCRIPTION

Figure 1:
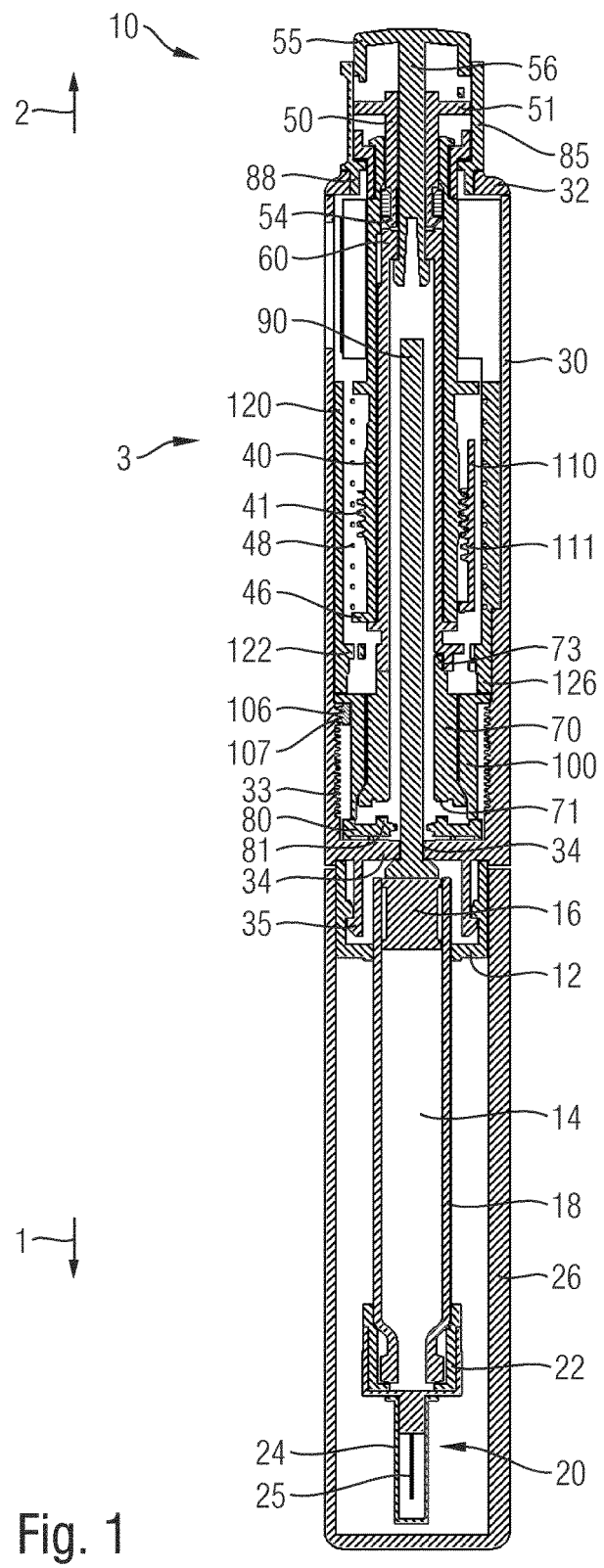
FIG. 1 schematically illustrates a drug delivery device in longitudinal cross-section.
Figure 2:
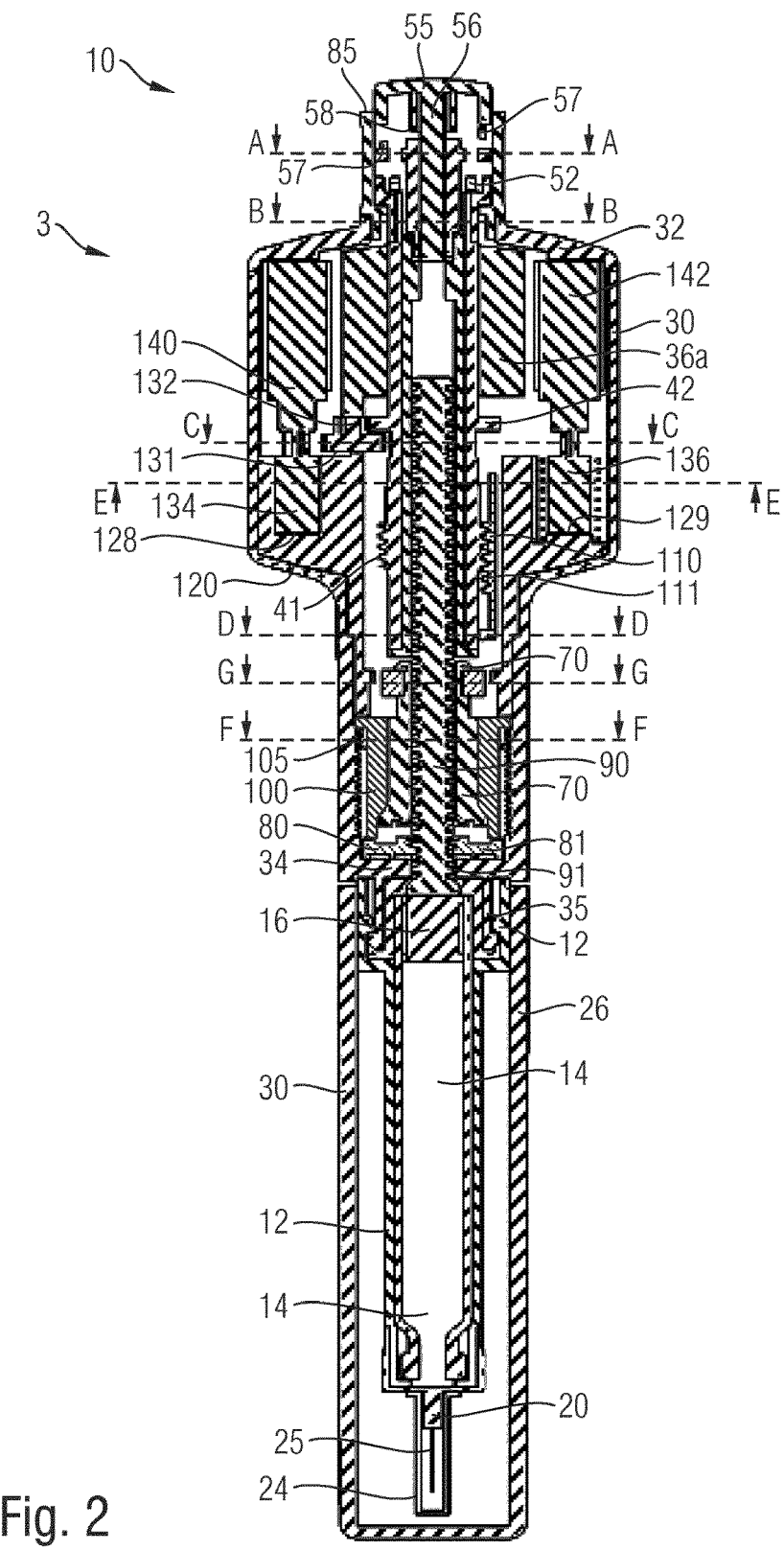
FIG. 2 shows another longitudinal cross-section of the drug delivery device rotated about 90° around its longitudinal axis.
Figure 10:
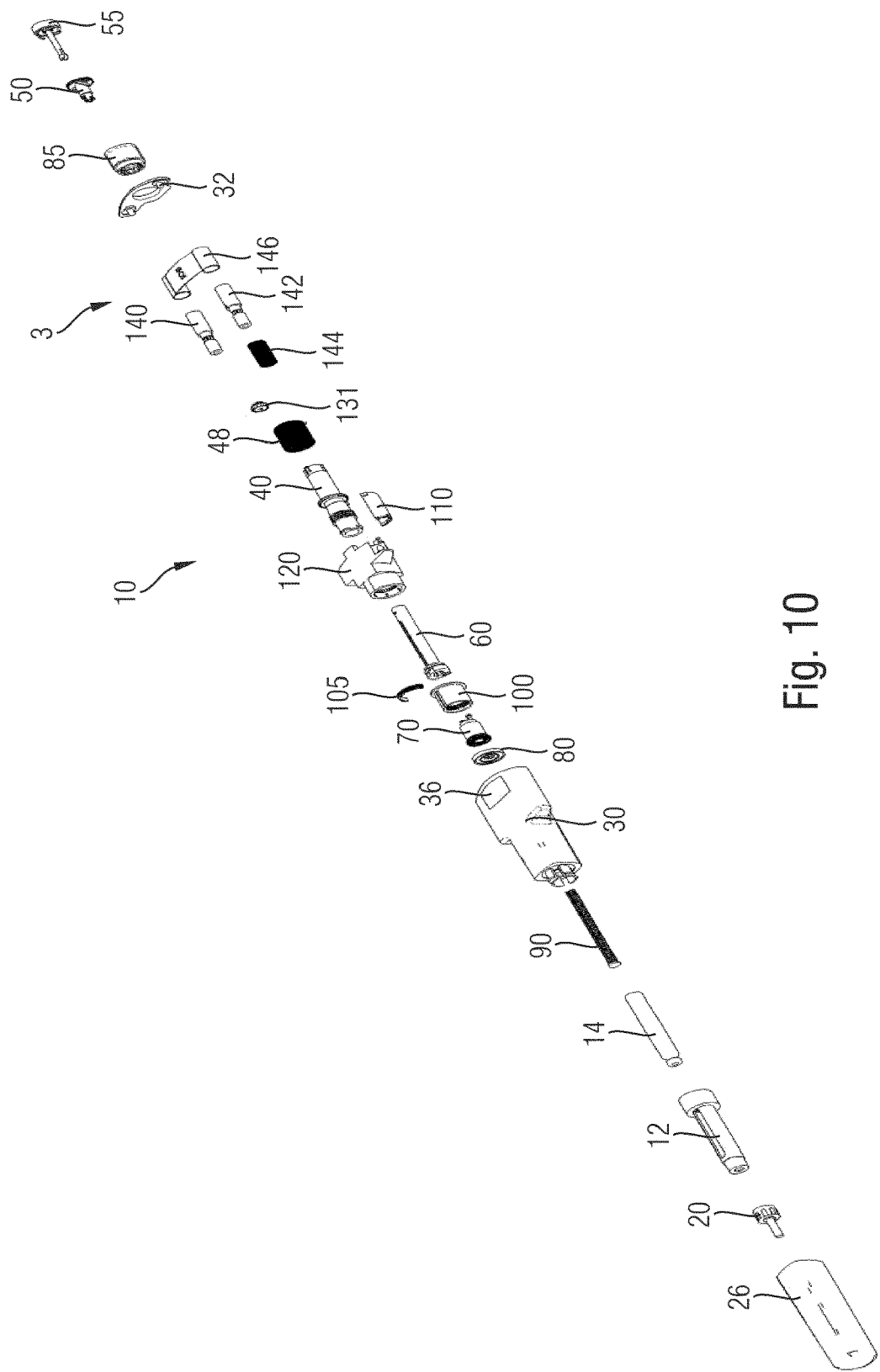
FIG. 10 shows an exploded view of the drug delivery device in perspective illustration.
Figure 11:
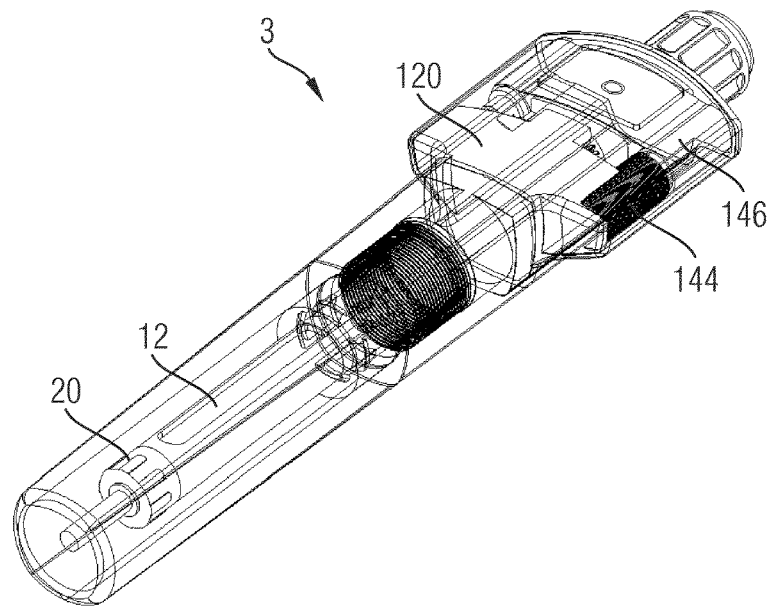
FIG. 11 shows a partially transparent view through the assembled drug delivery device.

In FIGS. 1, 2 and 10 the drive mechanism 3 of the drug delivery device 10 is illustrated in an assembled and in an exploded view, respectively. The drug delivery device 10 may be of pen-injector type and may comprise a substantially cylindrical and axially elongated shape. In the present set of Figures, the axial direction is denoted with reference number 1 and the opposite proximal direction is indicated by reference number 2. The drug delivery device 10 comprises a proximal housing component 30 to receive and to accommodate the drive mechanism 3 and in particular the functional and moveable components, the drive mechanism 3 is made of.

In distal direction 1, the housing 30 is connected with a cartridge holder 12 which is adapted to accommodate and to receive a cartridge 14 containing the medicament to be dispensed by the drug delivery device 10. The cartridge 14 typically comprises a vitreous barrel 18 of cylindrical shape which is sealed in distal direction 1 by a pierceable sealing member, such like a septum.

In proximal direction 2, the cartridge 14 is sealed by a piston 16 slidably arranged in the vitreous barrel 18 of the cartridge 14. Displacement of the piston 16 in distal direction 1 leads to a respective built-up of a fluid pressure inside the cartridge 14. When the distal outlet of a cartridge 14 is connected with e.g. a needle assembly 20, as shown in FIG. 1, a predefined amount of the liquid medicament contained in the cartridge 14 can be expelled and dispensed via an injection needle 25 of the needle assembly 22.

In FIG. 2 however, a needle cap 24 to protect the double-tipped injection needle 25 is indicated. The needle assembly 20 is typically arranged on a distal end portion of the cartridge holder 12. Typically, a distally located socket of the cartridge holder 12 and a needle hub 22 of the needle assembly 20 comprise mutually corresponding threads to screw the needle assembly 20 onto the cartridge holder 12 in a releasable and removable way.

The cartridge holder 12 and hence the cartridge 14 is to be protected and covered by a protective cap 26 which is shown in FIGS. 1 and 2. Prior to setting and/or dispensing of a dose, the protective cap 26 as well as the inner needle cap 24 are to be removed. After dispensing or injecting of the medicament into biological tissue, the needle assembly 20 is typically to be discarded and the distal end of the drug delivery device 10 is to be covered by the protective cap 26.

The drive mechanism 3 as illustrated in an exploded view in FIG. 10 and as shown in cross section in its fully assembled configuration in FIGS. 1 and 2 comprises numerous functional components by way of which a dose of variable size can be set and subsequently dispensed.

The dose dispensing procedure comes along with a distally directed advancing displacement of the piston rod 90 relative to the housing 30. The drive mechanism 3 therefore comprises at least a housing 30, a piston rod 90, a drive wheel 80 or drive nut and a drive sleeve 40 which can be selectively and operably coupled for setting and dispensing of a dose, respectively.

The dose dispensing procedure comes along with a distally-directed advancing displacement of the piston rod 90 relative to the housing 30. As illustrated for instance in FIG. 2, the piston rod 90 comprises an outer thread 91 which is typically rotatably locked to a radially inwardly extending support 34 of the housing 30. Advancing of the piston rod 90 in distal direction relative to the housing 30 is typically achieved by a rotation of the drive wheel 80 threadedly engaged with the piston rod 90 and being axially fixed in the housing 30.

In the following, setting of a dose is described.

For setting of a dose, a user typically takes the drug delivery device 10 and starts to rotate the proximally located dose setting member 85 relative to the proximal housing 30. Here, the dose setting member 85 comprises a dose dial, which is axially fixed to the housing 30 and which may be arbitrarily dialed either clockwise or counter-clockwise for incrementing and decrementing a dose to be set accordingly.

Figure 3:
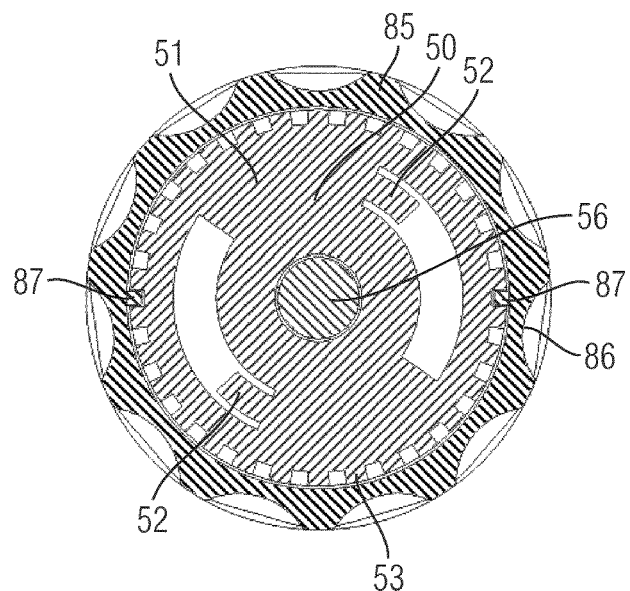
FIG. 3 shows a cross-section along A-A according to FIG. 2.

As in particular illustrated in FIG. 3, the dose setting member 85 comprises a rippled structure 86 at its outer circumference, which allows and supports a slip-free gripping and dialing thereof. Moreover, the dose setting member 85 has the form of a hollow sleeve and features two diametrically oppositely located and radially inwardly extending protrusions 87 engaging with a toothed geared rim 53 of a proximal clutch member 50 being rotatably supported in the housing 30.

As further illustrated in FIGS. 1 and 2, the housing 30 comprises a proximal closure or lid 32 which is axially intersected by the dose setting member 85, by the proximal clutch member 50 and by a dose dispensing button 55 proximally protruding from the dose setting member 85. As further indicated in FIGS. 1, 2 and in FIGS. 20, 21, the dose setting member 85 comprises a distally extending projection 88 of rim or ring-like shape extending into or through the proximal closure 32 of the housing 30. By means of the projection 88, the dose setting member 85 may be axially fixed to the housing 30.

The proximal clutch member 50 comprises or forms an axially extending shaft portion to axially and rotatably engage with a main clutch member 60 featuring a sleeve-like geometry. The proximal clutch member 50 typically comprises a fastening or fixing element 54 at its distal end of its shaft portion to rotatably and to axially engage with the main clutch member 60. In this way, a rotation of the proximal clutch member 50 typically induced by dialing of the dose setting member 85 can be equally and directly transferred into a respective rotation of the main clutch member 60.

Figure 5:
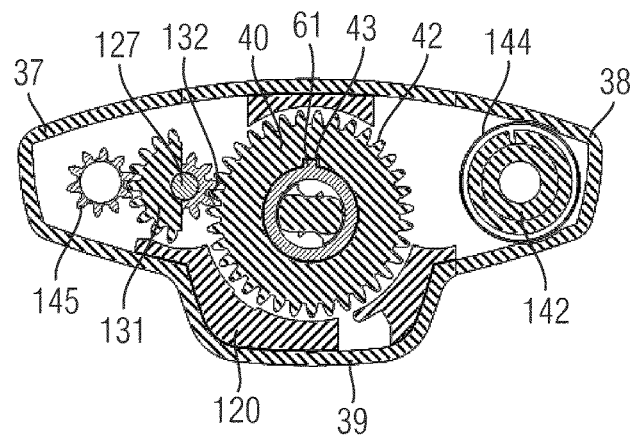
FIG. 5 shows a cross-section along C-C according to FIG. 2.
Figure 6:
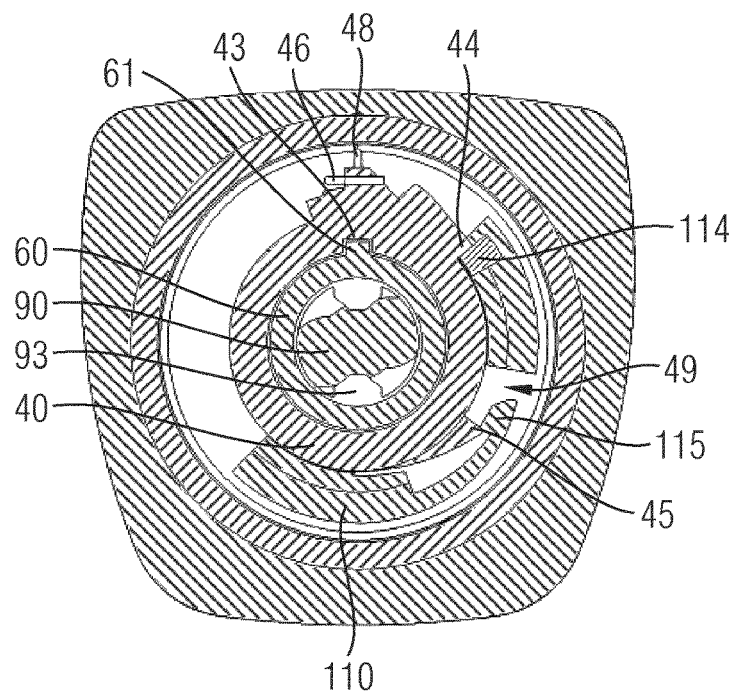
FIG. 6 shows a cross-section along D-D according to FIG. 2.

The main clutch member 60 is rotatably engaged with the drive sleeve 40 adapted to accommodate both, a distal end of the proximal clutch member 50 and almost the entirety of the main clutch member 60 extending almost all the way through the drive sleeve 40 in distal direction 1. As shown in FIGS. 5 and 6, the main clutch member 60 comprises a radially outwardly and axially extending ridge or protrusion 61 serving as a fastening element to rotatably engage with a correspondingly shaped groove or notch 43 provided at an inside facing portion of the drive sleeve 40.

By means of the radially outwardly extending protrusion 61 of the main clutch member 60 and the correspondingly shaped groove 43 of the drive sleeve 40, a splined engagement of main clutch member 60 and drive sleeve 40 can be provided. Consequently, the drive sleeve 40 and the main clutch member 60 are rotatably locked but the main clutch member 60 is free to be displaced in axial direction 1, 2 relative to the drive sleeve 40.

Figure 12:
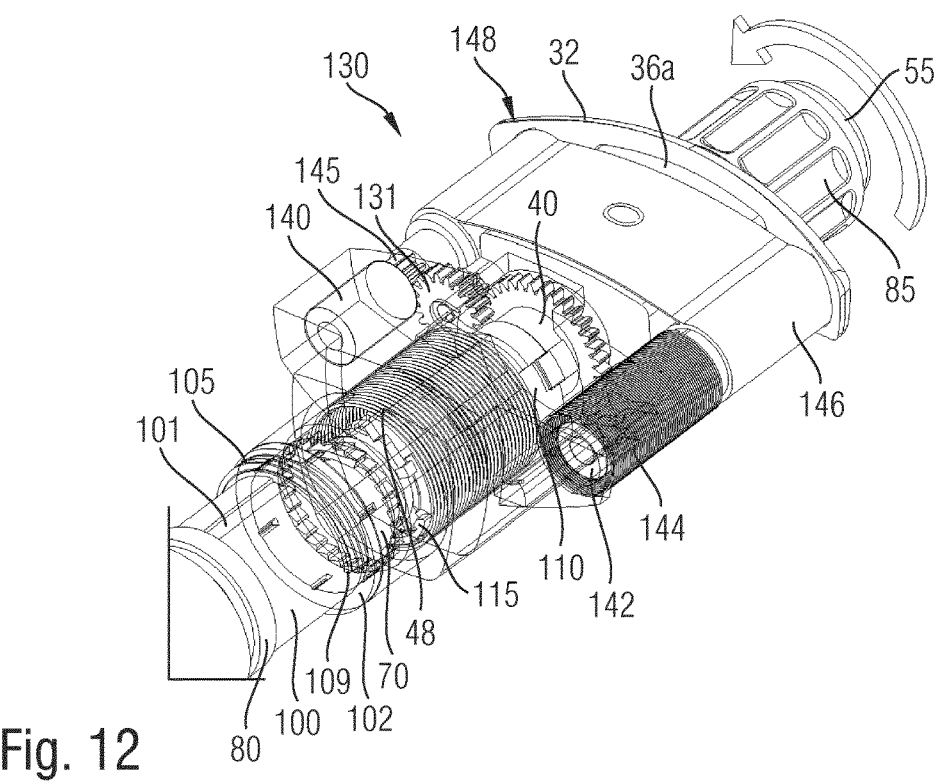
FIG. 12 is a perspective view of the dose indicating mechanism.

As illustrated in FIGS. 6 and 12 the drive sleeve 40 is connected with one end of a helical spring 48 extending around and enclosing the distal portion of the drive sleeve 40. The opposite end of the spring 48 is connected to an insert 120 which is fixedly connected to the housing 30. In this way, the drive sleeve 40 is rotatable in a dose incrementing direction 4 against the action of the helical spring 48.

Figure 9:
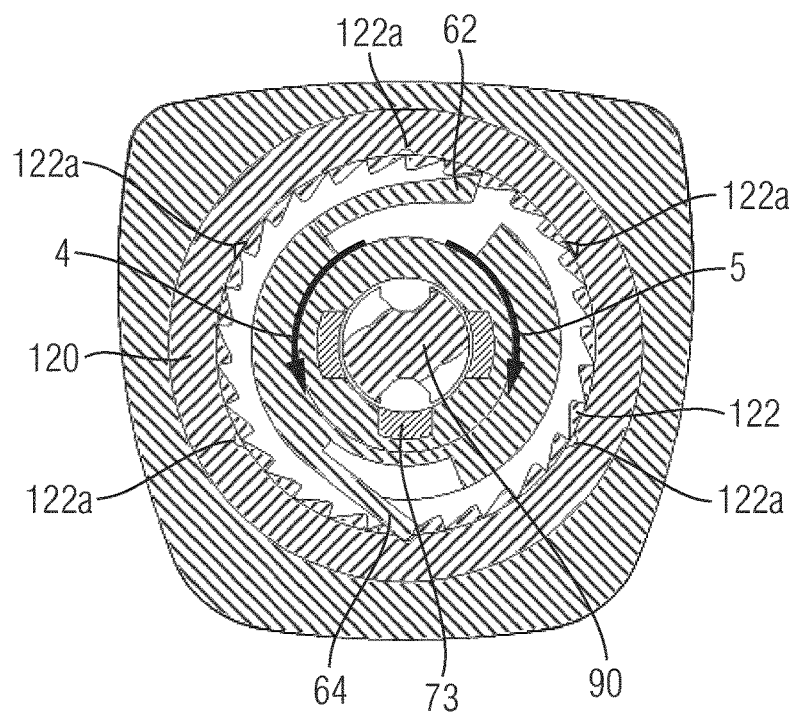
FIG. 9 shows a cross-section along G-G according to FIG. 2.

As further shown in FIG. 9 a pawl-like and radially outwardly extending ratchet member 62 is adapted to engage with a toothed ring portion 122 of the insert 120. The toothed ring 122 comprises a saw tooth profile such that the radially outwardly biased ratchet member 62 of the main clutch member 60 consecutively and stepwise engages with the toothed ring 122 in order to store and save mechanical energy of the strained helical spring 48 during a dose setting procedure. Here, the main clutch member 60 and the drive sleeve 40 rotatably locked therewith can be rotated in a dose incrementing direction 4 in discrete steps, e.g. corresponding to an international unit in case of a drug delivery device adapted for administering of insulin.

The engagement of the ratchet member 62 and the toothed ring 122 is such, that also a dose decrementing rotation 5 is possible when a respective torque is applied to the dose setting member 85 and hence to the main clutch member 60. The toothed flanks of the ratchet member 62 and the teeth of the toothed ring 122 are designed such, that also a well-defined and precise dose decrementing rotation of the main clutch member 60 and hence of the drive sleeve 40 is possible, in particular for correcting and for decrementing a dose that would be too large otherwise.

Figure 13:
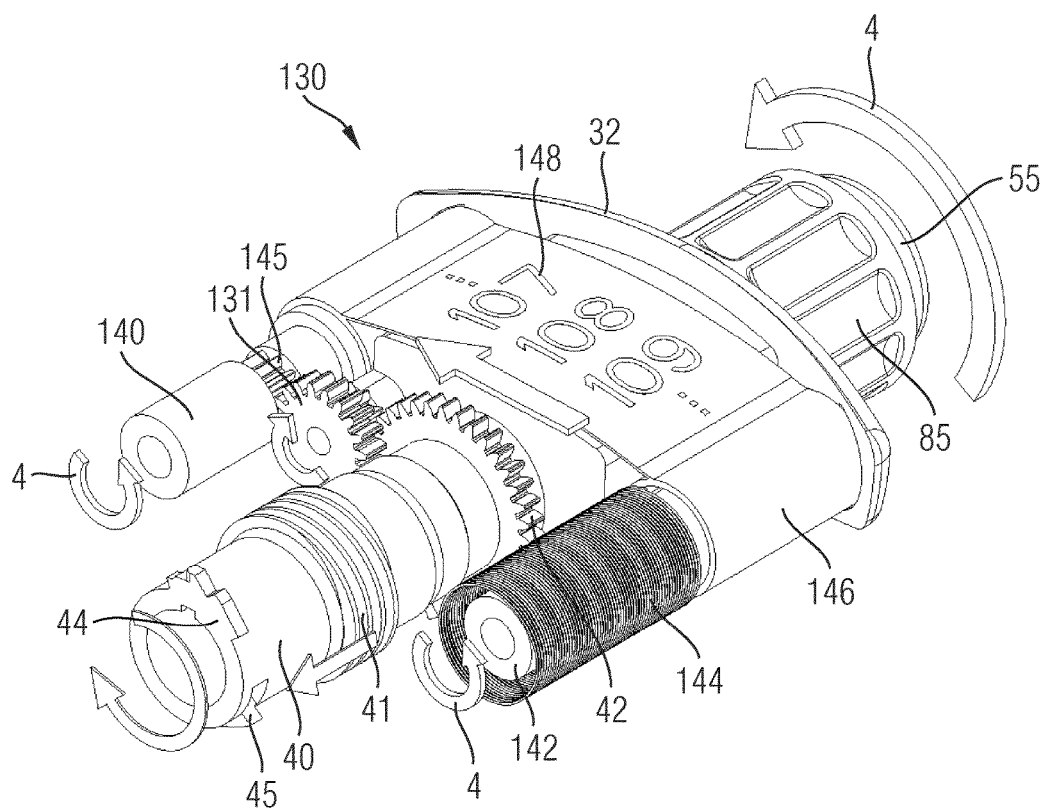
FIG. 13 shows an isolated view of the dose indicating mechanism.

As for instance illustrated in FIGS. 6, 7 and 12, 14 and 15 there is also provided a dose limiting member 110 acting as a single dose limiting member during a dose setting procedure. The dose limiting member 110 is threadedly engaged with the drive sleeve 40. As illustrated in FIG. 13, the drive sleeve 40 comprises only a limited axial portion provided with an outer thread 41. Said outer thread 41 is located offset from a distal end as well as from a proximal end of the drive sleeve 40. Adjacent to the threaded portion 41, the outer circumference of the drive sleeve 40 is rather smooth shaped.

Figure 7:
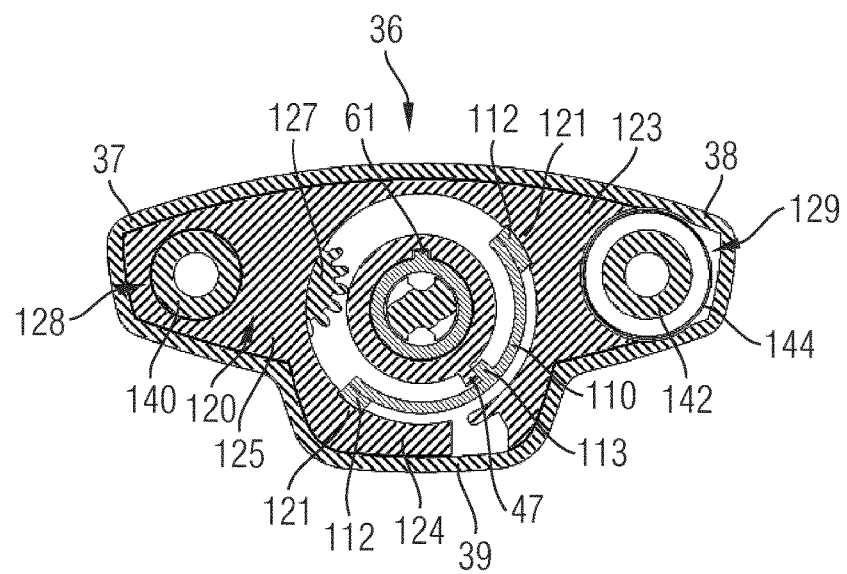
FIG. 7 shows a cross-section along E-E according to FIG. 2.

As shown in FIGS. 6 and 7, the dose limiting member 110 is of shell-like shape and extends only partially around the outer circumference of the drive sleeve 40. As further illustrated in FIG. 6, a distal end of the dose limiting member 110 extends radially between the drive sleeve 40 and the helical spring 48. Moreover, the distal end of the drive sleeve 40 comprises a radially outwardly extending spring mount 46 to engage with the distal end of the helical spring 48.

Figure 14:
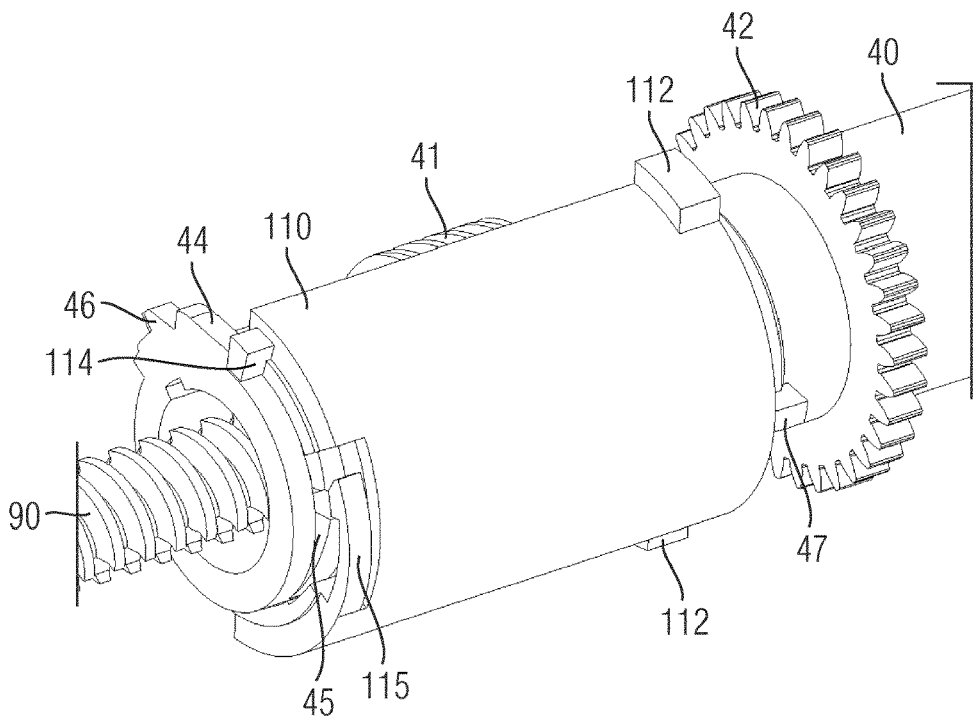
FIG. 14 shows the dose limiting member in a zero dose configuration on the drive sleeve.
Figure 15:
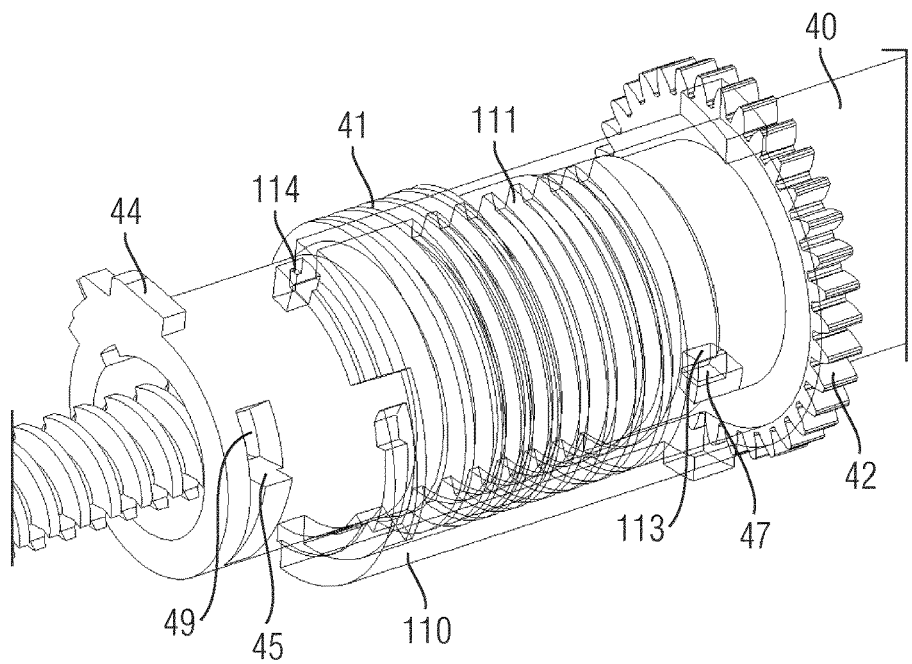
FIG. 15 shows the dose limiting member according to FIG. 14 in a maximum dose configuration.
Figure 16:
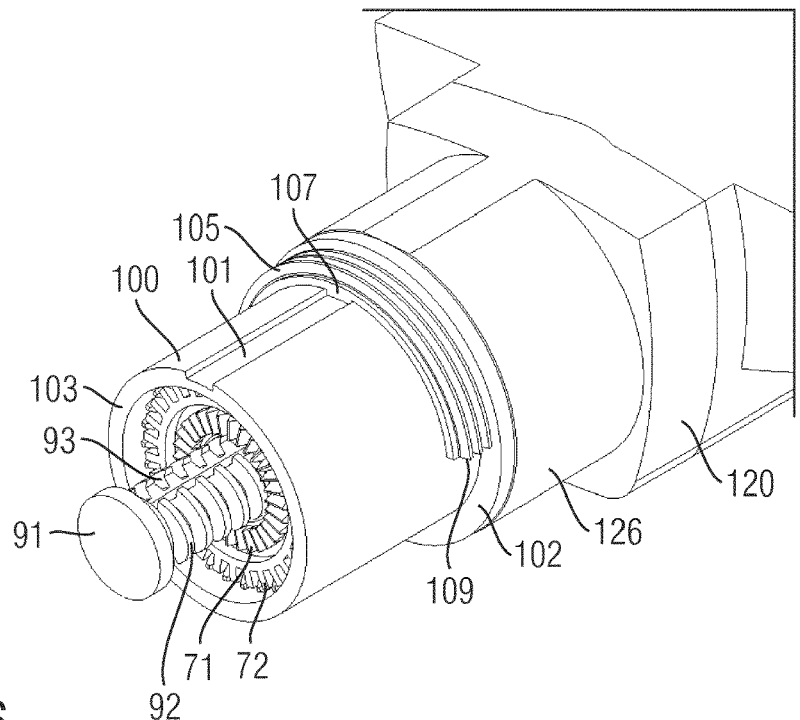
FIG. 16 shows a perspective view of a last dose limiting mechanism.

According to FIG. 15, the dose limiting member 110 comprises an inner thread 111 to engage with the outer threaded portion 41 of the drive sleeve 40. As further illustrated in FIGS. 7 and 14 the dose limiting member 110 comprises two diametrically oppositely located radially outwardly extending protrusions 112 engaging with correspondingly formed recesses 121 of the insert 120.

The cross-section according to FIG. 7 further illustrates that the insert 120 almost entirely fills the interior volume of the surrounding housing 30. Therefore, the insert 120 is fixedly connected to the housing 30 and serves as a housing portion to provide a mounting base for various functional components of the drive mechanism 3.

By means of mutually engaging protrusions 112 and grooves 121 the dose limiting member 110 is rotatably locked to the insert 120 and hence to the housing 30. Moreover, since the dose limiting member 110 is also threadedly engaged with the drive sleeve 40, a rotation of the drive sleeve 40 in dose incrementing direction 4, as illustrated in FIG. 24 leads to a proximally directed displacement of the dose limiting member 110. An oppositely directed rotation of the drive sleeve 40 in dose decrementing direction 5 leads to a respective opposite, hence distally directed displacement of the dose limiting member 110 relative to the insert 120, the housing 30 and relative to the drive sleeve 40 as illustrated in FIG. 25.

Moreover, FIGS. 7, 12, 14 and 15 show that the dose limiting member 110 comprises a radially inwardly extending first stop 113 near its proximal end which is adapted to circumferentially abut with a correspondingly shaped but radially outwardly extending first stop 47 of the drive sleeve 40. The configuration as indicated in FIGS. 7 and 15 may relate to a maximum dose configuration, in which the mutual abutment of first stops 47, 113 of drive sleeve 40 and dose limiting member 110 inhibits a further rotational displacement of the drive sleeve 40 in dose incrementing direction 4. In this way, a maximum dose for a single dose dispensing procedure can be effectively limited.

Later on and during dose dispensing or during dose correction, i.e. when the drive sleeve 40 is rotated in a dose decrementing direction 5, the dose limiting member 110 will be displaced in distal direction 1 in order to return into its initial zero dose configuration as it is indicated for instance in FIG. 14. Also here, mutually corresponding second stops 44, 114 of drive sleeve 40 and dose limiting member 110 are provided. While the second stop 44 of the drive sleeve 40 extends radially outwardly from a distally located rim of the drive sleeve 40 the second stop 114 of the dose limiting member 110 is located at a distal and circumferential edge of the shell-shaped dose limiting member 110. In particular, the second stop 114 is provided at a leading edge with respect to a rotation in dose decrementing direction 5.

In contrast to that, the first and radially inwardly extending stop 113 of the dose limiting member 110 extends substantially midway between the diametrically oppositely located radially outwardly extending protrusions 112. Moreover, the protrusions 112 and the first stop 113 are located in a common transverse plane as indicated in FIG. 7. In this way, forces or torque introduced into the dose limiting member 110 via the rotating drive sleeve 40 can be smoothly and directly transferred to the insert 120.

Since the dose limiting member 110 almost completely extends through the helical spring 48 in axial direction a rather compact and space saving arrangement for the dose limiting member 110 can be attained.

As further illustrated for instance in FIG. 12 the drive mechanism 3 also comprises a dose indicating mechanism 130 featuring first and second spools 140, 142 rotatably supported in the housing 30 and being oriented substantially parallel to each other as well as being oriented substantially parallel to the drive sleeve 40 and the piston rod 90 extending therethrough. The two spools 140, 142 are further mutually connected by means of a dose indicating tape 146 having several numbers 148 printed thereon.

As shown in FIGS. 2 and 12 the first spool 140 is rotatably engaged with the drive sleeve 40 by means of a series of gear wheels 42, 131. Here, the drive sleeve 40 comprises a gear wheel 42 that mates with a sprocket 132 of a gear wheel 131. Said gear wheel 131 is further geared and engaged with a corresponding gear wheel 145 of the first spool 140. In this way, a rotative movement of the drive sleeve 40 can be directly transferred into a roll off and roll up rotation of the first spool 140.

The second spool 142 is further engaged with a spool spring 144. In this way, unwinding or unrolling the dose indicating tape 146 from the second spool 142 may take place against the action of the spool spring 144. By means of the spool spring 144 the dose indicating tape 146 can be strained and can be kept substantially free of slack. Additionally and as shown in FIG. 12, the housing comprises a support 36a to provide a basis for the flexible dose indicating tape 146.

As further indicated in FIG. 2, the first spool 140 comprises a proximally located bobbin integrally formed with a distally located bearing portion 134. The bearing portion 134 is located and supported in a cup-shaped receptacle of the insert 120, thereby forming a bearing 128 for the first spool 140. In a corresponding way also the second spool 142 can be rotatably supported in the insert 120. As indicated in FIG. 7, the respective bearing portion 136 of the second spool 142 is only partially formed by an insert portion 123 of the insert 120.

The residual portion of the respective bearing 129 is formed directly from a radially outwardly extending receptacle portion 38 of the housing 30. As further indicated in FIGS. 2 and 7, the spool spring 144 radially extends between the outer circumference of the bearing portion 136, the inside facing sidewall portions of the insert portion 123 and the receptacle portion 38 of the housing 30.

As it is further illustrated in FIG. 7, the drug delivery device 10 in an axial portion comprises a T-like shape in cross-section to accommodate the dose indicating mechanism 130, wherein the two spools 140, 142 are located in receptacle portions 37, 38 being furthest away from each other. Therebetween and on one side there extends a radially outwardly extending receptacle portion 39 of the housing 30. Opposite the receptacle portion 39, the housing 30 comprises a dose indicating window 36 through which the numbers 148 of the dose indicating tape 146 can be visualised.

The lobe-shaped receptacle portions 37, 38 and 39 of the housing 30 are almost entirely occupied with correspondingly shaped insert portions 125, 123 and 124 of the insert 120, respectively.

Here, the insert 120 may provide a mounting basis to preassemble the dose indicating mechanism 130 and to insert the entire dose indicating mechanism 130 in one step into the housing 30 during assembly of the drug delivery device 10.

As further indicated in FIG. 5, also the gear wheel 131 is rotatably supported by a pin-shaped bearing 127 of the insert 120.

As further shown in FIGS. 2 and 10, the proximal closure 32 of the housing 30 provides axial fixing of the two spools 140, 142 inside the housing 30. Hence, the two spools 140, 142 can be axially constrained by the insert 120 and by the proximal closure 32 of the housing 30.

In FIGS. 2, 12 and in FIGS. 16 to 20 a last dose sleeve 100 rotatably supported in the housing 30 is shown. The last dose sleeve 100 comprises a radially outwardly extending flange portion 102 by way of which the last dose sleeve 100 axially abuts with a proximal sleeve portion 126 of the insert 120. Moreover, the last dose sleeve 100 comprises an axially extending groove 101 intersecting a rather smooth shaped outer circumference thereof.

Said groove 101 is engaged with a radially inwardly extending protrusion 107 of a last dose member 105, which is designed as a last dose nut or as a half nut. As for instance indicated in FIG. 18 the last dose member 105 comprises a semi-circular arcuate shape and features radial stop faces 108, 109 at its opposite circumferential ends. Moreover, the last dose member 105 comprises an outer thread 106 to threadedly engage with a correspondingly shaped threaded portion 33 of the housing 30. In this way, the last dose limiting member 105 is threadedly engaged with the housing 30 but is rotatably locked to the last dose sleeve 100.

Figure 4:
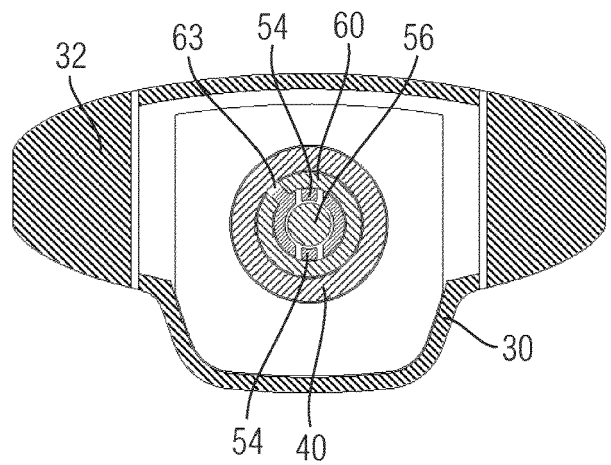
FIG. 4 shows a cross-section along B-B according to FIG. 2.
Figure 22:
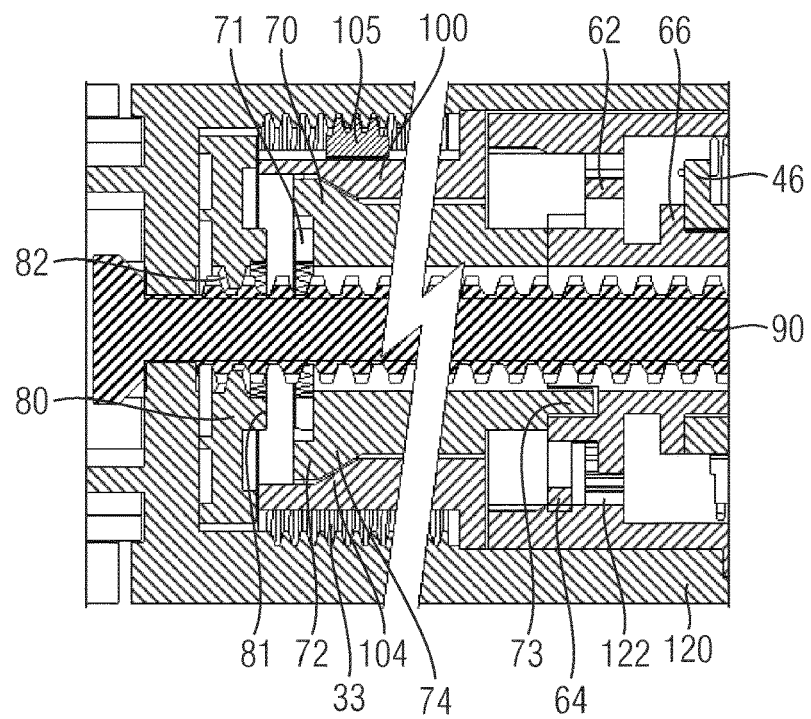
FIG. 22 shows a longitudinal cross-section through a distal clutch member in dose setting configuration.
Figure 23:
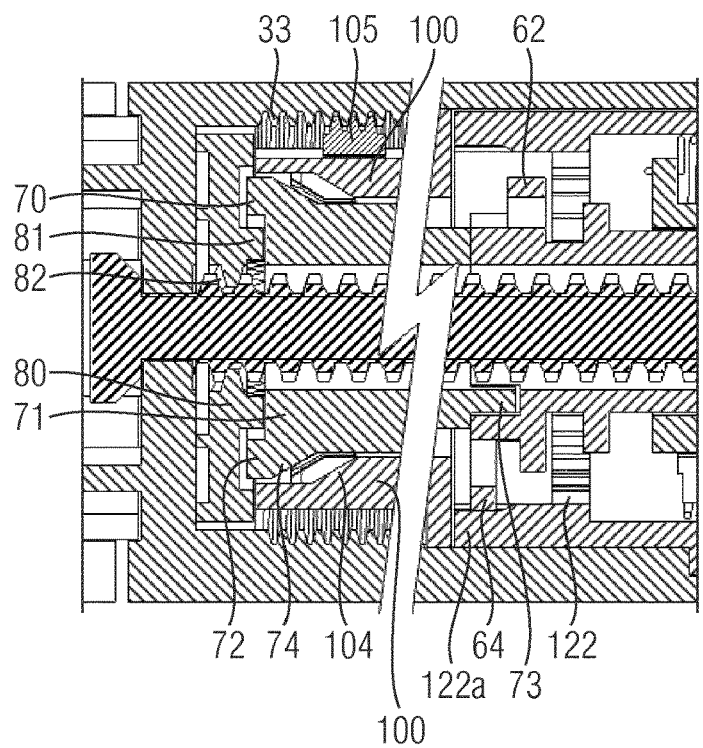
FIG. 23 shows a longitudinal cross-section of the distal clutch member in a dose dispensing configuration.

In FIGS. 1, 22 and 23 a distal clutch member 70 is illustrated, which is axially as well as rotatably engaged with the main clutch member 60. Hence, a rotation of the main clutch member 60 equally transfers to the distal clutch member 70. Moreover, also an axial displacement of the main clutch member 60 relative to the housing 30 or relative to the drive sleeve 40 is equally transferable to a respective axial displacement of the distal clutch member 70. In order to provide axial and rotational engagement between the main clutch with the distal clutch member 70 and/or with the proximal clutch 50 the main clutch 60 may further exhibit a notch or groove 63 as shown in FIG. 4 to engage with a correspondingly shaped snap member of e.g. the proximal clutch 50, which is not particularly illustrated. Moreover and as indicated in the cross sections of FIGS. 9 and 22 the distal clutch member 70 comprises three circumferentially distributed snap elements 73 to axially engage with correspondingly shaped recesses of the main clutch 60.

Figure 8:
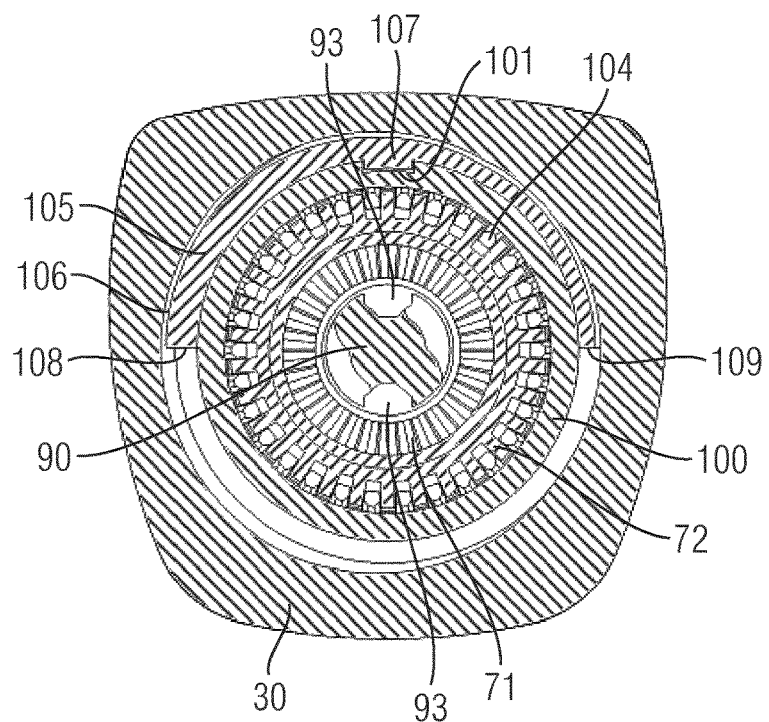
FIG. 8 shows a cross-section along F-F according to FIG. 2.

In a dose setting configuration as illustrated in FIG. 22, the distal clutch member 70 is rotatably locked to the last dose sleeve 100. As shown for instance in cross-section according to FIG. 8, the distal clutch member 70 comprises radially outwardly extending teeth 72 engaging with a correspondingly shaped toothed structure 104 at an inside facing sidewall portion of the last dose sleeve 100. In this way, a rotation of the drive sleeve 40 and hence a rotation of the clutch members 50, 60, 70 can transfer to a respective rotation of the last dose sleeve 100.

As a consequence, the last dose member 105 will travel in axial direction relative to the last dose sleeve 100 during a dose setting procedure. The lead of the threaded engagement of the last dose member 105 and the housing 30 as well as the axial elongation of the last dose sleeve 100 is designed such that a stop configuration as for instance illustrated in FIG. 19 correlates with the maximum allowable distal position of the piston rod 90 relative to the barrel 18 of the cartridge 14.

Figure 19:
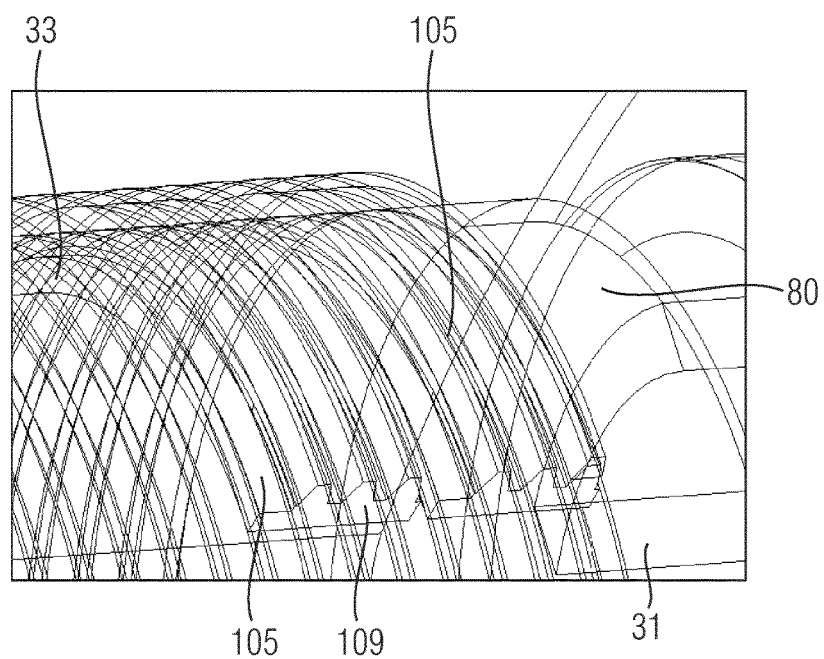
FIG. 19 shows a configuration of the last dose limiting mechanism in a last dose configuration.

In FIG. 19 mutual abutment of one of the stop faces 108, 109 with a radially inwardly extending stop 31 of the housing 30 is shown. Also here and in comparison with the single dose limiting member 110 radially extending stops 108, 109, 31 may provide a well-defined blocking of the mutually engaging components 105, 110 and housing 30.

Since the last dose sleeve 100 is only selectively coupled with the drive sleeve 40 and/or with the distal clutch member 70 during a dose setting procedure, the last dose member 105 will always rest in its axial position during a dose dispensing procedure.

Hence, during consecutive dose setting procedures, the last dose member 105 successively advances towards a last dose limiting configuration. In situations where the amount of medicament left in the cartridge 12 is less than the size of a single dose to be set during a dose setting procedure, the last dose limiting member 105 will be advanced in distal direction 1 and will engage with the radial stop 31 of the housing 30 thereby blocking a further rotation of the last dose sleeve 100 and hence of the clutches 50, 60, 70 and the dose setting member 85, accordingly. In this way it can be effectively prevented that a user selects and dials a dose exceeding the amount of medicament left in the cartridge 14.

In the following, dispensing of a dose is described.

Figure 17:
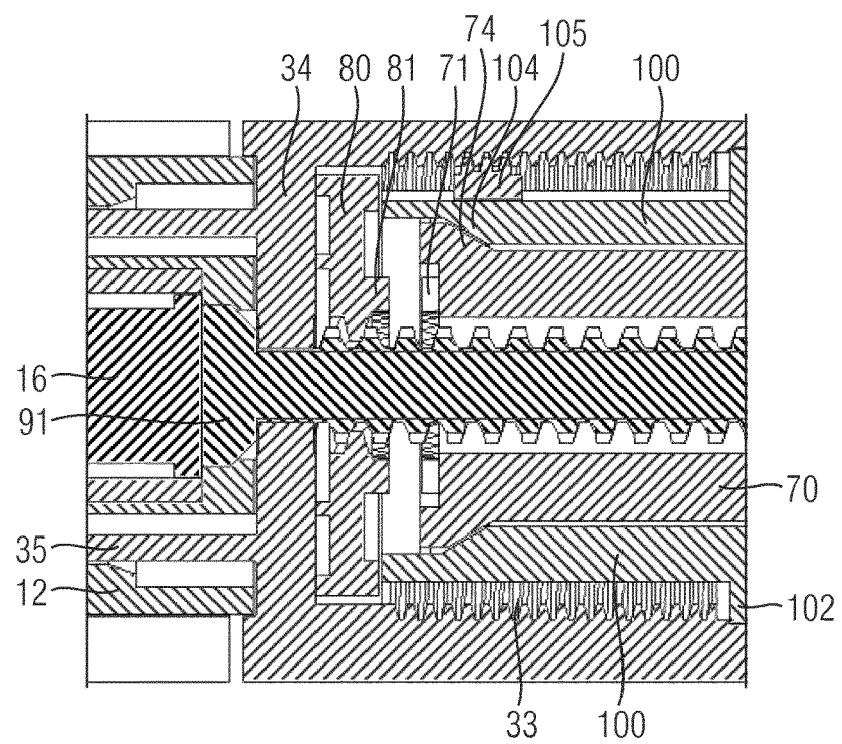
FIG. 17 shows an enlarged longitudinal cross-section through the last dose limiting mechanism.
Figure 18:
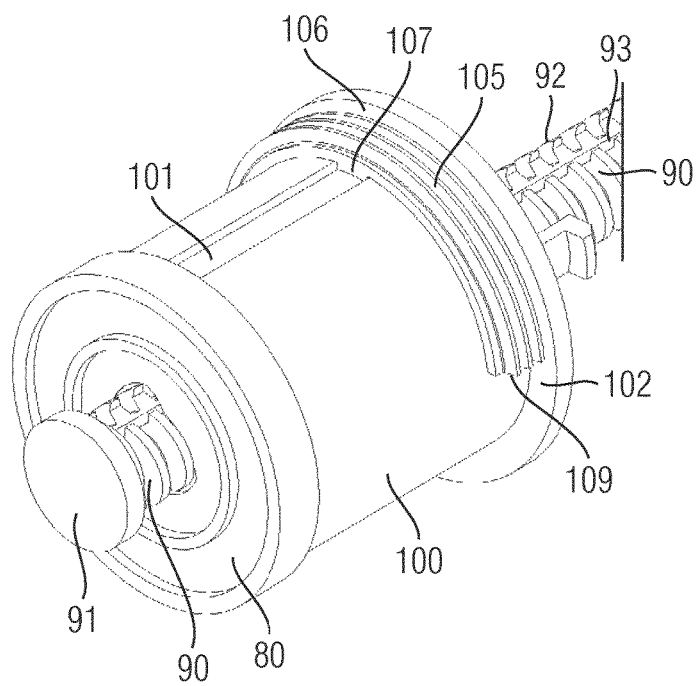
FIG. 18 shows another perspective view of the last dose limiting mechanism in a zero dose configuration.

As shown in FIG. 17, the piston rod or lead screw 90 operably engaged with a proximal end face of the piston 16 of the cartridge 14 is axially guided by the radially inwardly extending support 34 or web of the housing 30. As shown in cross section in FIG. 8, the piston rod 90 not only comprises an outer thread 92 but also two diametrically opposite and axially extending grooves 93. By means of said grooves 93 the piston rod 90 is rotatably locked to the housing 30. Hence, the piston rod 90 is splined to the housing 30. The piston rod 90 further comprises a radially widening pressure piece 91 or a pressure foot at its distal end in order to homogeneously transfer axially directed thrust to the piston 16 of the cartridge 14 during dose dispensing.

The piston rod 90 is further threadedly engaged with a drive wheel 80 comprising an inner thread 82 engaged with the outer thread 92 of the piston rod 90. Due to the threaded engagement with the drive wheel 80 and the splined engagement with the housing 30, the piston rod 90 experiences a distally directed translational displacement when the drive wheel 80 rotates in a dose decrementing direction 5 during dose dispensing. In order to transfer a dose dispensing torque to the drive wheel 80 or drive nut the drive wheel 80 comprises a crown wheel portion 81 at its proximally facing side to engage with a correspondingly shaped crown wheel portion 71 of the distal clutch member 70.

By displacing the distal clutch member 70 in distal direction 1 the mutually corresponding crown wheel portions 71, 81 of distal clutch member 70 and drive wheel 80 mutually engage. In this way, a rotation of the distal clutch member 70 can be equally transferred to a rotation of the drive wheel 80, which transfers to a distally directed displacement of the piston rod 90.

Figure 20:
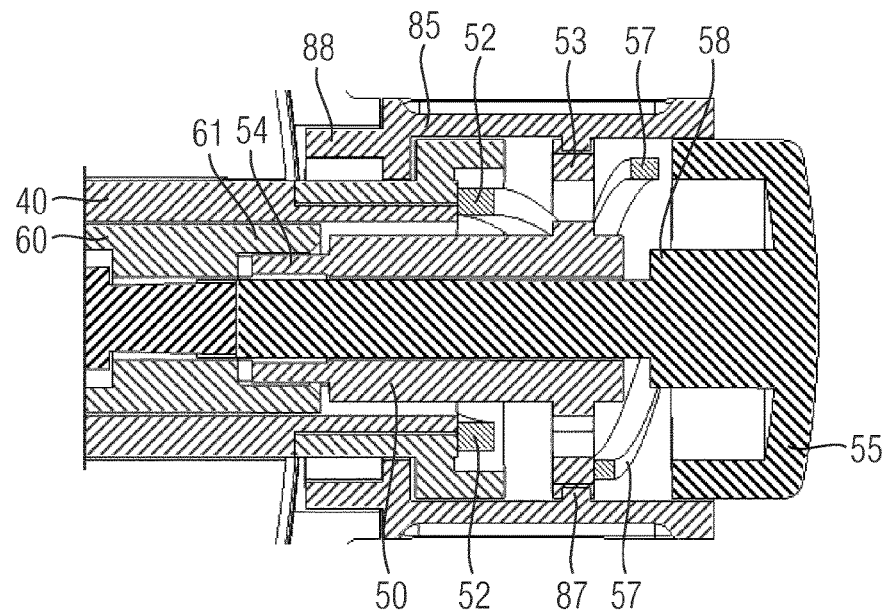
FIG. 20 shows a longitudinal cross-section through the proximal end of the drive mechanism in a dose setting configuration.
Figure 21:
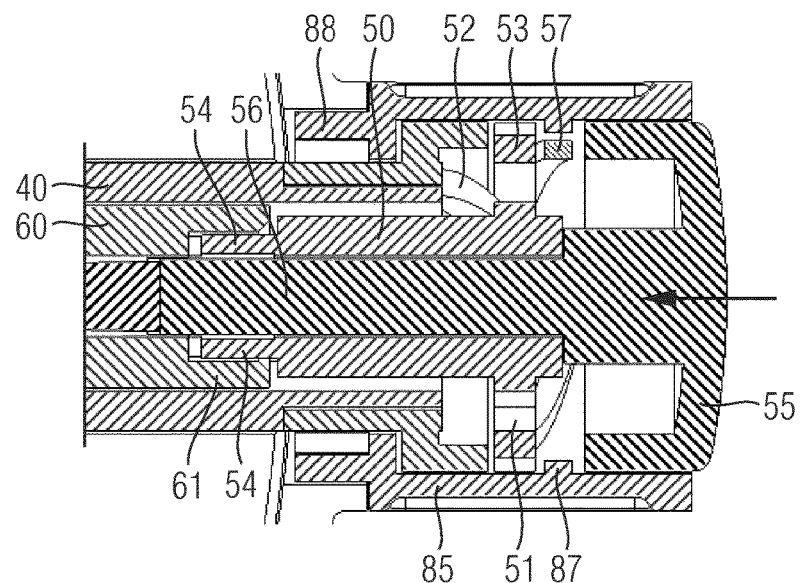
FIG. 21 shows a proximal end of the drive mechanism in a dose dispensing configuration.

A distally direction displacement of the distal clutch member 70 can be attained by depressing the dose dispensing button 55 in distal direction 1 as indicated by a comparison of FIGS. 20 and 21. The dose dispensing button 55 comprising a shaft portion 56 extending into the hollow shaft portion of the proximal clutch member 50 is displaceable in distal direction 1 until a stepped portion 58 radially outwardly extending from the shaft portion 56 axially abuts with a proximal end of the proximal clutch member 50.

In this way, axially and distally directed displacement of the dose dispensing button 55 against the action of an integrated spring 57 can be transferred into a respective distally directed displacement of the mutually engaging clutch members 50, 60 and 70. Since the clutch members 50, 60 and 70 are axially engaged in both directions, the proximal clutch member 50 can be displaced in distal direction 1 against the action of another integrated spring 52, which axially abuts with a proximal end face of the drive sleeve 40 and/or with a stepped portion of the dose setting member 85.

Distally directed displacement of the proximal clutch member 50 relative to the dose setting member 85 also disengages the protrusions 87 and the geared rim 53. In the dose dispensing configuration as shown in FIG. 21, the dose setting member 58 is therefore substantially functionless. It may be rotated in any direction without having connection to the proximal clutch member 50.

The proximal clutch member 50 is depressible in distal direction 1 against the action of the spring 52. Since the proximal clutch member 50 is axially engaged with the main clutch member 60, e.g. by means of a snap fit engagement, and since the main clutch member 60 is also axially connected with the distal clutch member 70, a release of the dose dispensing button 55 allows and induces a proximally directed return motion of the proximal clutch member 50 under the effect of the relaxing spring 52.

In this way, the distal clutch member 70 can be selectively engaged and disengaged with the drive wheel 80. Moreover, by means of the integrated spring 57 also the dose dispensing button 55 will return into its initial proximal end configuration in which the dose dispensing button 55 at least partially extends from the proximal end face of the dose setting member 85.

As shown in FIG. 20, the integrated spring 57 of the dose dispensing button 55 axially abuts against a radially outwardly extending flange portion 51 of the proximal clutch member 50.

By means of a distally directed displacement of the distal clutch member 70 the distal clutch member 70 not only rotatably locks to the drive wheel 80 but also disengages from the last dose sleeve 100 as becomes apparent from a comparison of FIGS. 22 and 23. As illustrated there, the last dose sleeve 100 comprises an inclined or tapered toothed structure 104 at its inner circumference near its distal end. Accordingly, the distal clutch member 70 comprises a correspondingly shaped inclined toothed portion 74 to engage with the toothed portion 104 of the last dose sleeve 100 when in dose setting configuration, hence when the distal clutch member 70 is in its proximal stop position.

As further indicated in FIG. 22 the ratchet member 62 of the main clutch 60 is rotatably locked to the toothed ring portion 122 of the insert 120. Additionally and as shown in FIG. 22 the main clutch 60 comprises a radially outwardly extending flange 66 which serves as a stop to engage with a distal end face of the drive sleeve 40. In this way the proximally directed displacement of the main clutch 60 under the effect of the springs 52, 57 can be delimited.

By displacing the three clutch members 50, 60, 70 simultaneously in distal direction 1, the crown wheel portion 71 of the distal clutch member 70 will engage with the corresponding crown wheel portion 81 of the drive wheel 80 before the ratchet member 62 disengages from the toothed ring portion 122 of the insert 120. The mutual engagement of the two crown wheel portions 71, 81 is designed such, that at least a further distally directed displacement of the distal clutch member 70 towards the drive wheel 80 is still possible when the distal clutch member 70 and the drive wheel 80 are already rotatably coupled.

During this further distally directed displacement of the distal clutch member 70 and when reaching the distal stop configuration, the ratchet member 62 displaces or has displaced in distal direction 1 relative to the toothed ring 122 and is then no longer inhibited to rotate under the action of the relaxing helical spring 48. As indicated in FIG. 23, the ratchet member 62 is disengaged from the insert 120 and hence it is effectively released from the housing 30.

The main clutch member 60 further comprises a pawl-shaped clicking member 64 as illustrated in FIGS. 9 and 23. Said clicking member 64 is arranged axially offset from the ratchet member 62. It may engage with another recessed structure 122a featuring numerous and equidistantly arranged recesses 122a located on the inside facing wall of the insert 120 when reaching the dose dispensing configuration as illustrated in FIG. 23.

The clicking member 64 is oriented symmetrically to the ratchet member 62 and engages with the recess structure 122a when the ratchet member 62 disengages from the toothed ring 122. Since the main clutch member 60 is now allowed to rotate in a dose decrementing direction 5 the clicking member 64 is operable to generate a frequent clicking sound when meshing with the recessed structure 122a, thereby audibly indicating to a user, that a dose dispensing procedure is in progress.

Moreover the clicking member 64 and the recessed structure 122a of the insert 120 may be shaped and designed in such a way that only a rotation in dose decrementing direction 5 is allowed while an oppositely directed rotation in dose incrementing direction 4 of the distal clutch 60 relative to the insert 120 and hence relative to the housing 30 is effectively blocked. In this way the clicking member 64 and the recessed structure 122a act as a further ratchet mechanism operable to impede a proximally directed displacement of the piston rod 90.

In order to provide a substantially slipless switching from dose setting mode to the dose dispensing mode and vice versa, the distal clutch member 70 engages with the drive wheel 80 before the main clutch member 60 disengages from the insert 120 or housing 30. Also in the event of a premature release of the dose dispensing button 55 during a dose dispensing procedure, a rotational interlock of the main clutch member 60 with the insert 120 will be re-established before distal clutch member 70 and drive wheel 80 become operably disengaged.

Since the drive sleeve 40 rotates in dose decrementing direction 5 during dose dispensing also the dose limiting member 110 will return into its initial configuration, i.e. in a zero dose configuration, in which the second stop 114 of the dose limiting member 110 engages with a radially extending second stop 44 of the drive sleeve 40.

Moreover, and as shown in FIG. 6, the dose limiting member 110 comprises a circumferentially extending clicking member 115 operable to audibly engage with a ledge 45 provided at a recess 49 of the drive sleeve 40. Here, the pawl-like clicking member 115 is biased radially inwardly so as to generate a click sound before or just when a zero dose configuration as illustrated in FIG. 6 is reached. Since the dose limiting member 110 travels in proximal direction 2 during dose incrementing rotation and travels in distal direction 1 during dose dispensing the audible click sound provided by the mutual engagement of the clicking member 115 with the ledge 45 is indicative to a user, that a dose dispensing procedure just terminates.

Accordingly and since the drive sleeve 40 is permanently engaged with the gear wheel 145 of the respective dose indicating mechanism 130, the numbers 148 of the dose indicating tape 146 that show up in the dose indicating window 36 will continuously count down until a zero dose configuration coinciding with the mutual engagement of the second stops 114, 44 is reached.

Moreover, as can be seen from the longitudinal cross-section according to FIG. 2, the drive wheel 80 is axially constrained between the radially inwardly extending protrusions 34 or of the housing and the last dose sleeve 100, which itself is in axial abutment with the distal sleeve portion 126 of the insert 120. In this way, fixing of the insert 120 in the housing 30 effectively fixes the last dose sleeve 100 and the drive wheel 80 in axial direction inside the housing 30.

Moreover, the insert 120 itself can be axially fixed in the housing 30 by means of the two spools 140, 142 extending axially between the bearing portion 128, 129 of the insert 120 and the proximal closure 32 of the housing 30.

As further shown in FIGS. 2 and 17, the housing 30 also comprises a distally extending appendix 35 extending in distal direction from the radially inwardly extending support 34. As indicated in FIG. 17, said appendix 35 may be operable to connect the proximal housing 30 with the cartridge holder 12. Cartridge holder 12 and housing 30 may either be releasably connected in order to provide a reusable drug delivery device, allowing to replace an empty cartridge 14 by a new one.

Alternatively, the drug delivery device 10 may also be designed as a disposable device, wherein cartridge holder 12 and proximal housing 30 are typically inseparably connected.

The present design and assembly of the components of the drive mechanism 3 allow for an axial adjustment of the piston rod 90 during a final step of assembly. In particular, prior to a final assembly of the dose dispensing button 55, effectively closing the housing 30 in proximal direction 2, the piston rod 90 is accessible by e.g. introducing an adjustment rod (not illustrated) through the hollow assembly of proximal clutch 50 and main clutch 60. In this way the piston rod 90 can be pushed in distal direction 1 to get in direct abutment with the piston 16 of the cartridge 14. In this way a conventional priming procedure typically to be executed by the end user prior to an initial use of the device 10 may become substantially superfluous.

The invention claimed is:

1. A drive mechanism of a drug delivery device for dispensing of a dose of a medicament, the drive mechanism comprising:
   a housing extending in an axial direction;
   a piston rod to operably engage with a piston of a cartridge to displace the piston in a distal direction;
   a drive sleeve extending in the axial direction and being rotatable in a dose incrementing direction against a force of a spring enclosing at least an axial portion of the drive sleeve;
   a dose limiting member threadedly engaged with the drive sleeve and rotatably locked to the housing, wherein at least a portion of the dose limiting member is located radially between the drive sleeve and the spring with respect to a longitudinal axis of the housing; and
   at least one stop located on at least one of the dose limiting member and the drive sleeve for limiting an axial displacement of the dose limiting member relative to the drive sleeve.

2. The drive mechanism of claim 1, wherein the dose limiting member and the housing comprise a radially outwardly extending protrusion configured to engage with a correspondingly shaped and axially extending groove.

3. The drive mechanism of claim 2, wherein the protrusion is axially offset from an axial end of the spring.

4. The drive mechanism of claim 1, wherein the dose limiting member comprises a shell-like profile extending only partially around a circumference of the drive sleeve, and oppositely located circumferential end sections of the dose limiting member each comprises a radially outwardly extending protrusion.

5. The drive mechanism of claim 4, wherein the dose limiting member comprises a first radially inwardly extending stop configured to engage with a first radially outwardly extending stop of the drive sleeve when the dose limiting member reaches a dose limiting configuration.

6. The drive mechanism of claim 5, wherein the first stop of the dose limiting member extends substantially midway between the radially outwardly extending protrusions of the oppositely located circumferential end sections of the dose limiting member.

7. The drive mechanism of claim 6, wherein the dose limiting member comprises a second stop at a circumferential and axial edge thereof to engage with a radially outwardly extending second stop of the drive sleeve.

8. The drive mechanism of claim 7, wherein the first radially inwardly extending stop and the second stop of the dose limiting member are located at opposite axial end sections of the dose limiting member.

9. The drive mechanism of claim 5, wherein the first radially outwardly extending stop of the drive sleeve is located axially offset from an outer thread of the drive sleeve.

10. The drive mechanism of claim 1, wherein the dose limiting member comprises a resilient, circumferentially extending clicking member to audibly engage with a correspondingly shaped recess or ledge of the drive sleeve before or when a stop of the dose limiting member engages with a corresponding stop of the drive sleeve.

11. The drive mechanism of claim 1, wherein the drive sleeve is rotatably engaged with a dose indicating mechanism comprising a first spool and a second spool rotatably supported in the housing at a predefined distance in a substantially parallel orientation, wherein a dose indicating tape coiled onto the second spool is fixed with an end to an outer circumference of the first spool.

12. The drive mechanism of claim 11, wherein the housing is adapted to receive an insert providing a bearing for at least one of first and second spools and/or providing at least one axially extending groove to engage with a protrusion of the dose limiting member.

13. The drive mechanism of claim 11, wherein the second spool is rotatable against a force of a coil spring and wherein the first spool is permanently rotatably engaged with the drive sleeve.

14. The drive mechanism of claim 1, wherein:
the drive sleeve is axially fixed relative to the housing,
the drive sleeve is hollow, and
at least one axially extending clutch member extending through the drive sleeve is rotatably locked to the drive sleeve and is axially displaceable relative to the drive sleeve to selectively engage with a drive wheel engaged with the piston rod for driving the piston rod in the distal direction.

15. The drive mechanism of claim 1, further comprising a first stop located near a proximal end of the dose limiting member, and a second stop located near a distal end of the dose limiting member, the first and second stops configured to limit an axial displacement of the dose limiting member relative to the drive sleeve.

16. A drug delivery device for dispensing of a dose of a medicament, comprising:
a drive mechanism comprising
a housing extending in an axial direction,
a piston rod to operably engage with a piston of a cartridge to displace the piston in a distal direction,
a drive sleeve extending in the axial direction and being rotatable in a dose incrementing direction against a force of a spring enclosing at least an axial portion of the drive sleeve,
a dose limiting member threadedly engaged with the drive sleeve and rotatably locked to the housing, wherein at least a portion of the dose limiting member is located radially between the drive sleeve and the spring with respect to a longitudinal axis of the housing, and
at least one stop located on at least one of the dose limiting member and the drive sleeve for limiting an axial displacement of the dose limiting member relative to the drive sleeve; and
a cartridge at least partially filled with the medicament and being arranged in the housing of the drive mechanism or in a cartridge holder fixed to the housing.

17. The drug delivery device of claim 16, wherein the dose limiting member and the housing comprise a radially outwardly extending protrusion configured to engage with a correspondingly shaped and axially extending groove.

18. The drug delivery device of claim 17, wherein the protrusion is axially offset from an axial end of the spring.

19. The drug delivery device of claim 16, wherein the dose limiting member comprises a shell-like profile extending only partially around a circumference of the drive sleeve, and oppositely located circumferential end sections of the dose limiting member each comprises a radially outwardly extending protrusion.

20. The drug delivery device of claim 19, wherein the dose limiting member comprises a first radially inwardly extending stop configured to engage with a first radially outwardly extending stop of the drive sleeve when the dose limiting member reaches a dose limiting configuration.

21. The drug delivery device of claim 20, wherein the first radially inwardly extending stop of the dose limiting member extends substantially midway between the radially outwardly extending protrusions of the oppositely located circumferential end sections of the dose limiting member.

22. The drug delivery device of claim 16, further comprising a first stop located near a proximal end of the dose limiting member, and a second stop located near a distal end of the dose limiting member, the first and second stops configured to limit an axial displacement of the dose limiting member relative to the drive sleeve.

* * * * *